(12) United States Patent
Miesenböck et al.

(10) Patent No.: US 7,144,733 B2
(45) Date of Patent: Dec. 5, 2006

(54) BIO-SYNTHETIC PHOTOSTIMULATORS AND METHODS OF USE

(75) Inventors: Gero Miesenböck, New York, NY (US); Boris V. Zemelman, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 324 days.

(21) Appl. No.: 10/222,675

(22) Filed: Aug. 16, 2002

(65) Prior Publication Data

US 2003/0040080 A1    Feb. 27, 2003

Related U.S. Application Data

(60) Provisional application No. 60/345,741, filed on Dec. 31, 2001, provisional application No. 60/312,707, filed on Aug. 16, 2001.

(51) Int. Cl.
*C12N 15/63*  (2006.01)
*C12N 15/85*  (2006.01)
*C12N 15/87*  (2006.01)
*A01N 35/00*  (2006.01)
*A61K 31/11*  (2006.01)

(52) U.S. Cl. ...................... 435/455; 514/703

(58) Field of Classification Search ............ 435/320.1, 435/455, 456; 514/44, 703; 424/93.21, 424/93.2
See application file for complete search history.

(56) References Cited

U.S. PATENT DOCUMENTS

2002/0123464 A1    9/2002  Kapeller-Libermann ..... 514/12
2003/0013137 A1*   1/2003  Barak et al. ................ 435/7.21

OTHER PUBLICATIONS

Jindrova, Physiol. Res. 47: 155-168, 1998.*
Pulvermuller, Biochemistry, 36:9253-9260, 1997.*
Neves et al. Science, 295:1636-1639, 2002.*
Anderson et al., Nature, vol. 392, pp. 25-30, 1998.*
Verma, Nature, vol. 389, pp. 239-242, 1997.*
Kmiec, American Scientist, 1999, 87, 240-247.*
Juengst, BMJ, 2003, 326:1410-11.*
Orkin et al., Dec. 7, 1995, "Report and Recommendation of the Panel to Assess the NIH investment in Research and Gene Therapy", issued by the National Institute of Health.*
Oakley et al. The Journal of Biological Chemistry 275:17201-17210, 2000.*
Scott, K. et al. *G q α Protein Function In Vivo: Genetic Dissection of Its Role in Photreceptor Cell Physiology: Neuron*, vol. 15, Oct. 1995, pp. 919-927.
Chappell S.A., et al. *A 9-nt Segment of a Cellular MRNA can Function as an Internal Ribosome Entry Site (IRES) and When Present in Linked Multiple Copies Greatly Enhances IRES Activity: Scripps Research Institute and Skaggs Institute for Chemical Biology.*, Feb. 2000, vol. 97, No. 4, pp. 1536-1541.
Bibikov, S. I. et al. *Bacteriorhodopsin is involved in halobacterial Photoreception: Proc. Natural Acadamy Science*, Oct. 1993, vol. 90, pp. 9446-9450.
Zemelman, B.V. et al. *Selective Photostimulation of Genetically ChARGed Neurons: Neuron*, Jan. 2002, vol. 33, pp. 15-22.

* cited by examiner

*Primary Examiner*—Brian Whiteman
(74) *Attorney, Agent, or Firm*—Marina Larson & Associates, LLC

(57) ABSTRACT

Cells are rendered sensitive to stimulation by introducing into a non-photoreceptor cell nucleic acid sequences encoding at least an opsin gene product, an arrestin gene product, and the alpha subunit of the heterotrimeric G protein of the $G_q$ family. The introduced sequences are expressed by the cell to yield at least the opsin gene product, the arrestin gene product, and the alpha subunit of the heterotrimeric G protein of the $G_q$ family. Retinal or a derivative thereof capable of bonding with the opsin gene product to form a rhodopsin is provided to the cell. The cell is then irradiated with light having a wavelength capable of converting the rhodopsin to metarhodopsin. The conversion of rhodopsin to metarhodopsin triggers a cascade of intracellular responses within the cell resulting in an increased intracellular concentration of $IP_3$ and calcium ions.

11 Claims, 14 Drawing Sheets pGal4 -- 3 independent fly lines pUAS -- 1 fly line carrying all the silent genes

BIO-SYNTHETIC PHOTOSTIMULATORS AND METHODS OF USE

CROSS-REFERENCE TO RELATED APPLICATIONS

The present application claims the benefit under 35 U.S.C. 119(e) of U.S. Provisional Patent Application Ser. No. 60/312,707, filed Aug. 16, 2001, and U.S. Provisional Patent Application Ser. No. 60/345,741, filed Dec. 31, 2001; the disclosures of which are incorporated herein by reference.

FEDERAL FUNDING LEGEND

This invention was made using federal funds under Grant No. 08748 by the National Cancer Institute. Accordingly, the Government has certain rights in this invention.

BACKGROUND OF THE INVENTION

1. Field of the Invention

The present invention relates generally to the fields of cellular biochemistry and neurophysiology. Generally, the present invention relates to techniques for optically stimulating genetically designated cells throughout the body. More specifically, it relates, inter alia, to techniques for direct activation of neural circuits by optically stimulating groups of genetically designated neurons.

2. Description of the Related Art

Little is known about the architecture of neuronal circuits controlling brain functions. It is unclear how neuronal cells act in concert to encode and convey information or what roles different types of cells in various regions of the brain play in processing and shaping that information. The ability to address such questions would significantly further the understanding of brain function and will better equip medical researchers to devise treatments for brain-related disorders. Unfortunately, both in vivo and in vitro techniques available currently are insufficient.

One in vivo technique used to provide information about brain function involves stimulating an experimental subject with a sensory stimulus, such as a smell, a sound, an image, etc., and measuring the electrical response in the brain with externally positioned electrodes. Alternatively, instead of measuring the response electrically, the response to the stimulus may be observed using functional magnetic resonance imaging (fMRI).

Although such in vivo techniques are helpful in identifying certain general areas correlated with particular brain functions, these techniques typically do not enable one to identify the cellular elements of specific neuronal pathways.

In contrast, various in vitro techniques permit the identification of individual neurons linked in neuronal pathways present within tissue samples or networks made up of mixed ensembles of neuronal cells. However, they do not help to determine what role, if any, those pathways play in the intact animal. For a summary of various in vitro techniques see, e.g., Crick, "The impact of molecular biology on neuroscience," *Phil. Trans. R. Soc. Lond. B*, 354:2021–5 (1999) and Zemelman et al., "Genetic schemes and schemata in neurophysiology," *Current Opinion in Neurobiology*, 11:409–14 (2001).

One in vitro technique for identifying neuronal pathways involves a microelectrode search for neurons presynaptic to a given neuron. This technique typically involves impaling a first neuron with a first microelectrode and impaling a second neuron with a second microelectrode. The first microelectrode is then used to electrically stimulate the first neuron. The second microelectrode is used to measure any electrical response from the second neuron resulting from stimulation of the first neuron. The first microelectrode is then switched from the first neuron to a number of other neurons, and this stimulation and response procedure is repeated for each such neuron tested. This technique can be, however, both time and labor intensive, and often results in the incomplete elucidation of neuronal pathways, leads to the stimulation of axons of passage, and causes mechanical disturbance or destruction of the tissue.

Another in vitro method for identifying neuronal pathways is disclosed in Farber et al., "Identification of Presynaptic Neurons by Laser Photostimulation," *Science*, 222:1025–7 (1983). This method comprises administering a fluorescent dye to all the cells in a neural tissue sample. A neuron present within the neural tissue sample is impaled with a microelectrode, and a laser microbeam is used to illuminate a stained neuron of interest, causing the illuminated neuron to fire an action potential. A synaptic response to the photostimulated neuron by the impaled neuron is then measured using the microelectrode. The response of the impaled neuron to a number of other stained neurons in the tissue sample is then tested by using the laser microbeam to sequentially illuminate other stained neurons.

Unfortunately, the Farber method is based on the light-induced formation of small pores in the neuronal membrane resulting from the photoexcitation of the fluorescent dye. (The pores act as ion channels, resulting in depolarization of the affected cell and the subsequent firing by the affected cell of an action potential.) As a result, a given cell can be photostimulated only a small number of times before it is killed by phototoxic damage. In addition, the fluorescent dye used in Farber has been found to vary in performance for different cell types and is occasionally species-specific.

Callaway et al. (*Proc. Natl. Acad. Sci USA*, 90:7661–5 (1993)) discloses another in vitro method for identifying neuronal pathways. The Callaway method involves treating a neural tissue sample with L-glutamic acid (4,5-dimethoxy-2-nitrobenzyl) ester. L-glutamic acid (4,5-dimethoxy-2-nitrobenzyl) ester is a caged or inactive form of the neurotransmitter glutamate and is capable of being converted to glutamate using ultraviolet irradiation. The locations of neurons making functional synaptic connections to a neuron of interest are then revealed by recording electrical activity from the neuron of interest while sequentially irradiating other neurons in the sample.

One shortcoming of the in vitro techniques described above that involve photostimulation (e.g., the Farber technique and the Callaway technique) is that the photostimulation must be confined to a single cell at any given point in time in order to permit an accurate determination of the presynaptic neuron responsible for exciting the electrically-monitored neuron, while in many systems neurons are known to carry information by acting in concert. However, the individual photostimulation of a large number of neurons present in a neural tissue sample can be time and labor intensive and cannot be used to target multiple cells simultaneously.

Another shortcoming of these photostimulation techniques is that they require the use of synthetic indicators or caged compounds, which are difficult to apply to intact tissues or organisms.

Lastly, the brain is typically not homogenous in terms of cell type, but is made up of different types of neurons that are physically arranged in a manner that combines regularity on a large scale with a significant degree of local variability, with neurons of a given cell type typically forming neuronal pathways with other neurons of the same or different cell type. However, such variations in cell type do not always result in easily identifiable visual differences among various cell types. Consequently, although it is often desirable to examine particular cell types in neuronal pathways or networks, it is often impossible to identify these desired cell types for stimulation. This makes application of the above-described photostimulation techniques all the more difficult.

The prior art is deficient in the lack of effective techniques for, inter alia, stimulating groups of neurons or neural circuits in intact tissue or an intact animal system for the purposes of analysis or intervention. The present invention fulfills this long-standing need and desire in the art.

SUMMARY OF THE INVENTION

The present invention, in one embodiment, provides a method of sensitizing a cell to light, comprising the steps of: (a) introducing into the cell a nucleic acid encoding an opsin gene product, a nucleic acid encoding an arrestin gene product, and a nucleic acid encoding the alpha subunit of a heterotrimeric G protein; so that the opsin gene product, the arrestin gene product, and the alpha subunit of a heterotrimeric G protein are expressed in the cell; and (b) supplying the cell with retinal or a derivative of retinal so as to convert the opsin gene product into a rhodopsin. In one aspect, the nucleic acid encoding an opsin gene product comprises an invertebrate, e.g., insect, opsin gene. A representative example of a useful opsin gene is a *Drosophila melanogaster* ninaE gene. In one aspect, the nucleic acid encoding an arrestin gene product comprises an invertebrate arrestin gene. A representative example of a useful arrestin gene is a *Drosophila melanogaster* arrestin-2 gene. In one aspect, the alpha subunit of a heterotrimeric G protein is the alpha subunit of a heterotrimeric $G_q$ protein. More particularly, a useful nucleic acid encoding the alpha subunit of a heterotrimeric G protein comprises a Gqα gene. A representative example of a Gqα gene is a *Drosophila melanogaster* Gqα gene. In another aspect, the alpha subunit of a heterotrimeric G protein is the alpha subunit of a heterotrimeric $G_s$ protein. In another aspect, the alpha subunit of a heterotrimeric G protein is the alpha subunit of a heterotrimeric $G_i$ protein. In yet another aspect, the alpha subunit of a heterotrimeric G protein is a chimeric alpha subunit of a heterotrimeric G protein. In the methods of the present invention, each nucleic acid is operatively linked to a promoter or an internal ribosome entry site (Chappell, Edelman et al. "A 9-nt segment of a cellular mRNA can function as an internal ribosome entry site (IRES) and when present in linked multiple copies greatly enhances IRES activity," *Proc Natl Acad Sci USA* 1536–41. (2000)) that is active in the selected cell.

In the methods of the present invention, retinal or a derivative of retinal may be used to convert the opsin gene product into a rhodopsin. In one aspect, the derivative of retinal is 3-hydroxyretinal. In another aspect, the derivative of retinal is retinol or retinyl ester, which are bioconverted by the cell to retinal.

The methods of the present invention may further comprise the step of introducing into the cell a fourth (or more) nucleic acid encoding a gene product selected from the group consisting of NinaA, the α subunit of a heterotrimeric G-protein, the βγ subunits of a heterotrimeric G-protein, NorpA, TRP, TRPL, InaD, TRPC3 (or other vertebrate TRP channels), inositol-1,4,5-trisphosphate ($IP_3$) receptor, trun- cated $IP_3$ receptor, a TRP-$IP_3$ receptor chimera, RdgA, or any of the gene products in Table 1.

Although the introduction of the nucleic acids into the target cell may be by any suitable means, representative methods include transfection, infecting the cell with a virus comprising the nucleic acid sequences, microinjecting the nucleic acid sequences into the cell, or generating transgenic animals. In one aspect, the invention comprises transfecting the cell with one or more different species of plasmids. For example, as described in detail below, two plasmids may be used: one plasmid may be pChARGe-1 and the second plasmid may be pChARGe-2. Alternatively, two viruses may be used, based on the vectors pvChARGe 1 and 2 or pvChARGe 1 and 3, to infect the cells simultaneously. Alternatively still the genes could be introduced into cells through transgenesis, by incorporating the chARGe genes into the genomes of animal cells and breeding transgenic animals.

Using the methods described by the present invention, a person having ordinary skill in this art would be able to sensitize a cell to photostimulation. Although a preferred cell is a neuron, or nerve cell, these techniques may be used to photosensitize, for example, a mast cell, a blood platelet, a liver cell, a fat cell, a pancreatic islet cell, an adrenal chromaffin cell, a C cell, a T-cell, a smooth muscle cell, a taste bud cell, a hormone or polypeptide secreting cell, a contractile cell, a smooth muscle cell, a striated muscle cell or a malignant cell.

The present invention, in another embodiment, provides a method of photostimulating a non-photoreceptor cell, comprising the steps of: (a) introducing into the cell a nucleic acid encoding an opsin gene product, a nucleic acid encoding an arrestin gene product, and a nucleic acid encoding the alpha subunit of a heterotrimeric G protein; so that the opsin gene product, the arrestin gene product, and the alpha subunit of a heterotrimeric G protein are expressed in said cell; (b) supplying said cell with retinal or a derivative thereof so as to convert said opsin gene product into a rhodopsin; and (c) illuminating the cell with light having a wavelength capable of transforming said rhodopsin into a metarhodopsin whereby said metarhodopsin activates said heterotrimeric G protein.

The present invention, in another embodiment, provides a method for stimulating a cell or group of cells within an explanted tissue sample, including cell culture, comprising the steps of: (a) sensitizing a cell type to photostimulation; (b) illuminating an area of the tissue sample with light capable of photostimulating only said sensitized cell type; and (c) monitoring the resultant activity in sensitized and/or non-sensitized cells within the tissue sample.

The present invention, in another embodiment, provides a method for stimulating a cell or group of cells within a tissue in situ, comprising the steps of: (a) sensitizing a cell type within the tissue to photostimulation; (b) illuminating an area of the tissue with light capable of photostimulating only said sensitized cell type; and (c) monitoring the resultant activity in sensitized and/or non-sensitized neurons within the tissue.

The present invention, in another embodiment, provides a method of identifying a neuronal pathway within a neural tissue sample, comprising the steps of: (a) sensitizing a cell type within the neural tissue sample to photostimulation; (b) illuminating an area of the neural tissue sample with light capable of photostimulating only said sensitized cell type; and (c) monitoring the resultant activity in sensitized and/or non-sensitized neurons within the neural tissue sample.

The present invention, in another embodiment, provides a method for stimulating a neuronal cell or group of cells that have been shown, through analysis of neuronal activity, to participate in neuronal pathways implicated in sensation and perception, movement, arousal, addiction, attention, emotion, and homeostasis, language, thought, learning, and memory, comprising the steps of: (a) introducing a sensor (such as a genetically encodable or exogenously added sensor) of neuronal activity into the neurons or subset of neurons of a responding animal; (b) challenging said animal with a stimulus or task expected to provoke neural activity, or establishing a mental state, such as enumerated above; (c) monitoring the activity of the sensor to determine which cells respond to the applied stimulus; (d) sensitizing said cells within the neural tissue of the same or different animal to photostimulation using promoters known to drive gene expression only in said cells within the neural tissue; (e) illuminating an area of the neural tissue with light capable of photostimulating only said sensitized cell type; and (f) monitoring the resultant behavior or neuronal activity in sensitized and/or non-sensitized cells within the neural tissue.

The present invention, in another embodiment, provides a method for stimulating neuronal pathways that have been implicated in sensation and perception, movement, arousal, addiction, attention, emotion, and homeostasis, language, thought, learning, and memory in an intact animal comprising the steps of: (a) sensitizing cells or sets of cells within the neural tissue of the animal to photostimulation by using promoters known to drive gene expression only in said neurons or sets of neurons; (b) illuminating an area of the neural tissue with light capable of photostimulating only sensitized cell type; and (c) monitoring the resultant behavior of the animal (Crawley and Paylor "A proposed test battery and constellations of specific behavioral paradigms to investigate the behavioral phenotypes of transgenic and knockout mice," *Horm Behav* 197–211. (1997); Crawley "Behavioral phenotyping of transgenic and knockout mice: experimental design and evaluation of general health, sensory functions, motor abilities, and specific behavioral tests," *Brain Res* 18–26. (1999)).

The present invention, in another embodiment, provides a method for implicating novel neuronal pathways in sensation and perception, movement, arousal, addiction, attention, emotion, and homeostasis, language, thought, learning, and memory in an intact animal comprising the steps of: (a) randomly sensitizing cells or sets of cells within the neural tissue of the animal to photostimulation by using gene trapping (Leighton, Mitchell et al. "Defining brain wiring patterns and mechanisms through gene trapping in mice," *Nature* 174–9. (2001)); (b) illuminating an area of the neural tissue with light capable of photostimulating only sensitized cell type; and (c) monitoring the resultant behavior of the animal.

The present invention, in another embodiment, provides a method for stimulating neuronal cells within the human body implicated in sensation and perception, movement, arousal, addiction, attention, emotion, and homeostasis, language, thought, learning, and memory comprising the steps of: (a) sensitizing cells or sets of cells within the human neural tissue to photostimulation by using promoters known to drive gene expression only in said neurons or sets of neurons; (b) illuminating an area of the neural tissue with light capable of photostimulating only sensitized cell type; and (c) monitoring or altering the behavior of the treated individual.

The present invention, in yet another embodiment, provides an expression vector, comprising a *Drosophila* opsin gene operatively linked to a first promoter, an arrestin-2 gene operatively linked to a second promoter and a Gqα gene operatively linked to a third promoter, with each promoter supporting either a general or a cell- or tissue-specific gene expression pattern.

The present invention, in yet another embodiment, provides an expression vector, comprising an opsin gene, an arrestin gene, and a Gqα gene operatively linked to a promoter or an internal ribosome entry site (Chappell, Edelman et al. "A 9-nt segment of a cellular mRNA can function as an internal ribosome entry site (IRES) and when present in linked multiple copies greatly enhances IRES activity," *Proc Natl Acad Sci USA* 1536–41. (2000)), allowing two or more genes to use the same promoter, and with the promoter supporting either a general or a cell- or tissue-specific gene expression pattern.

The present invention, in yet another embodiment, provides a viral expression vector (Naldini, Blomer et al. "In vivo gene delivery and stable transduction of nondividing cells by a lentiviral vector," *Science* 263–7. (1996); Blomer, Naldini et al. "Highly efficient and sustained gene transfer in adult neurons with a lentivirus vector," *J Virol* 6641–9. (1997); Kafri, Blomer et al. "Sustained expression of genes delivered directly into liver and muscle by lentiviral vectors," *Nat Genet* 314–7. (1997); Miyoshi, Blomer et al. "Development of a self-inactivating lentivirus vector," *J Virol* 8150–7. (1998); Federico "Lentiviruses as gene delivery vectors," *Curr Opin Biotechnol* 448–53. (1999); Olefsky "Diabetes. Gene therapy for rats and mice," *Nature* 420–1. (2000)), comprising an opsin gene operatively linked to a first promoter, an arrestin gene operatively linked to a second promoter and a Gqα gene operatively linked to a third promoter, with each promoter supporting either a general or a cell- or tissue-specific gene expression pattern.

The present invention, in yet another embodiment, provides a viral expression vector, comprising an opsin gene, an arrestin gene, and a Gqα gene operatively linked to a promoter or an internal ribosome entry site, allowing two or more genes to use the same promoter, and with the promoter supporting either a general or a cell- or tissue-specific gene expression pattern.

The present invention, in yet another embodiment, provides a transgenic non-human animal (Lois, Hong et al. "Germline transmission and tissue-specific expression of transgenes delivered by lentiviral vectors," *Science* 868–72. (2002)) whose genome comprises (a) a first transgene comprising an opsin gene operatively linked to a first promoter, (b) a second transgene comprising an arrestin gene operatively linked to a second promoter, and (c) a third transgene comprising the alpha subunit of a heterotrimeric G protein operatively linked to a third promoter, wherein said first, second and third promoters support either a general or a cell- or tissue-specific gene expression pattern.

The present invention, in yet another embodiment, provides a transgenic non-human animal whose genome comprises (a) a first transgene comprising an opsin gene, (b) a second transgene comprising an arrestin gene, and (c) a third transgene comprising the alpha subunit of a heterotrimeric G protein, wherein one or more of the genes is operatively linked to a cell-specific or general promoter and the remaining genes are positioned directly behind the first and preceded by internal ribosome entry site sequences, thereby operatively linking them also to the same promoter.

The present invention, in yet another embodiment, provides a viral expression vector for use in humans, for example in gene therapy applications (Yamada, Takeuchi et al. "A 49-kilodalton phosphoprotein in the *Drosophila* photoreceptor is an arrestin homolog," *Science* 483–6 (1990); Somia and Verma "Gene therapy: trials and tribulations," *Nat Rev Genet* 91–9. (2000); Wu and Ataai "Production of viral vectors for gene therapy applications," *Curr Opin Biotechnol* 205–8. (2000)), whose genome comprises (a) a first transgene comprising an opsin gene operatively linked to a first promoter, (b) a second transgene comprising an arrestin gene operatively linked to a second promoter, and (c) a third transgene comprising the alpha subunit of a heterotrimeric G protein operatively linked to a third promoter, wherein said first, second and third promoters support either a general or a cell- or tissue-specific gene expression pattern.

The present invention, in yet another embodiment, provides a viral expression vector for use in humans, for example in gene therapy applications, whose genome comprises (a) a first transgene comprising an opsin gene, (b) a second transgene comprising an arrestin gene, and (c) a third transgene comprising the alpha subunit of a heterotrimeric G protein, wherein one or more of the genes is operatively linked to a cell-specific or general promoter and the remaining genes are positioned directly behind the first and preceded by internal ribosome entry site sequences, thereby operatively linking them also to the same promoter.

The present invention, in yet another embodiment, provides an expression vector for use in humans in conjunction with non-viral gene delivery technologies, such as lipid-mediated cell transfection technologies and others, for example in gene therapy applications, whose genome comprises (a) a first transgene comprising an opsin gene operatively linked to a first promoter, (b) a second transgene comprising an arrestin gene operatively linked to a second promoter, and (c) a third transgene comprising the alpha subunit of a heterotrimeric G protein operatively linked to a third promoter, wherein said first, second and third promoters support either a general or a cell- or tissue-specific gene expression pattern.

The present invention, in yet another embodiment, provides an expression vector for use in humans in conjunction with non-viral gene delivery technologies, such as lipid-mediated cell transfection technologies and others, for example in gene therapy applications, whose genome comprises (a) a first transgene comprising an opsin gene, (b) a second transgene comprising an arrestin gene, and (c) a third transgene comprising the alpha subunit of a heterotrimeric G protein, wherein one or more of the genes is operatively linked to a cell-specific or general promoter and the remaining genes are positioned directly behind the first and preceded by internal ribosome entry site sequences, thereby operatively linking them also to the same promoter.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1 shows the reconstitution of *Drosophila* phototransduction in *Xenopus* oocytes: delineation of the minimal chARGe: and the three essential genes identified as the *Drosophila* arrestin-2 gene, the ninaE opsin gene, and the dgq G alpha gene. Oocytes were exposed to 40 µM synthetic all-trans retinal for 15 min, membrane potentials were clamped to −80 mV, and transmembrane currents recorded during periods of darkness (shaded backgrounds) and white illumination (white backgrounds). Inward currents are displayed as downward deflections from baseline; the zero time point is defined as the onset of the light stimulus. Oocytes were programmed to express: (FIG. 1A, right) the minimal chARGe, consisting of NinaE, arrestin-2, and Gα.

FIG. 4 shows the photostimulation of chARGed hippocampal neurons. Periods of darkness and white illumination are indicated by shaded and white backgrounds, respectively.

FIG. 5 shows the intensity and wavelength dependence of photostimulation.

FIG. 7 shows generally the process of creating transgenic animals and specifically the process of generating transgenic Drosophila melanogaster fly lines carrying and expressing chARGe genes.

FIG. 8 shows examples of chARGe constructs that may be used to create identifiable chARGed cells within transgenic animals.

DETAILED DESCRIPTION OF THE INVENTION

Figure 1A:
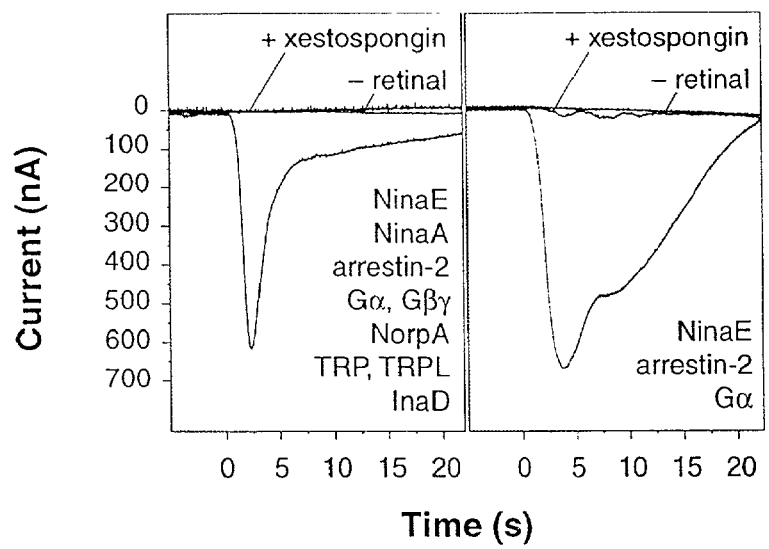
(FIG. 1A, left) a "complete" set of 10 phototransduction proteins, consisting of NinaE, NinaA, arrestin-2, Gα, Gβγ, NorpA, TRP, TRPL, and InaD.

The present invention is based, in part, on the insight that a non-photoreceptor cell can be sensitized to photostimulation. For example, the present invention is directed to a method of sensitizing a cell to light by (a) introducing nucleic acid sequences encoding at least an opsin gene product, an arrestin gene product, and the alpha subunit of the heterotrimeric G protein of the $G_q$ family into the cell so as to express the nucleic acid sequences; and (b) providing the cell with retinal or a derivative thereof so as to convert the opsin gene product into a rhodopsin. Thus sensitized to light, the cell can then be photostimulated with light of an appropriate wavelength to undergo a change in intracellular second messenger concentration, thereby triggering a variety of secondary effects associated with such an increase. The nucleic acid sequences for the aforementioned opsin gene product, arrestin gene product and $G_q$ are preferably derived from the fruit fly, Drosophila melanogaster, where the subject gene products are believed to be involved in the visual transduction cascade occurring in Drosophila photoreceptor cells.

For information regarding Drosophila visual transduction, see Montell, "Visual Transduction in Drosophila," Annu. Rev. Cell Dev. Biol., 15:231–68 (1999).) The phototransduction cascade is initiated by the absorption of light by the photopigment rhodopsin. Rhodopsin comprises (i) an opsin moiety containing seven transmembrane segments and (ii) a chromophore in the form of 3-hydroxyretinal covalently bound to a lysine residue in the seventh transmembrane domain of the opsin moiety. A number of different opsin gene products have been identified in Drosophila, many of the opsin gene products having a spectrally distinguishable absorption maximum. Absorption of a photon of light by the chromophore results in conversion of the 11–12 double bond in 3-hydroxyretinal from a cis configuration to a trans configuration and, thereby, results in the conversion of rhodopsin into its activated isomer, i.e., metarhodopsin.

Metarhodopsin then interacts with and activates the heterotrimeric GTP-binding protein $G_q$. Activated $G_q$ activates phospholipase C (PLC), which in turn catalyzes the conversion of phosphatidylinositol-4,5-bisphosphate ($PIP_2$) to inositol-1,4,5-trisphosphate ($IP_3$) and diacylglycerol (DAG). Inositol-1,4,5-trisphosphate then stimulates the release of calcium ions from intracellular reserves located in the endoplasmic reticulum of the Drosophila photoreceptor cells by binding to $IP_3$-gated calcium ion release channels present in the endoplasmic reticulum membrane. Diacylglycerol and/or its metabolites interact with membrane-bound effector proteins. How the generation of these second messenger molecules leads to the depolarization of the cell is presently unclear. According to one theory, the release of calcium ions from the endoplasmic reticulum triggers the opening of the cation influx channels TRP (transient receptor potential) and TRPL (transient receptor potential-like), thereby leading to an influx of cations, such as $Na^+$ and $Ca^{2+}$, and resulting in depolarization of the photoreceptor cell. According to another theory, the cation influx channels transient receptor potential and transient receptor potential-like, are activated directly by a metabolite of diacylglycerol, such as a polyunsaturated fatty acid. According to yet another theory, receptors interact directly with transient receptor potential-like channels in the plasma membrane and can open those channels in response to $IP_3$, depolarizing the plasma membrane.

TABLE I lists many of the genes and corresponding gene products that have been identified as being involved in the Drosophila visual transduction cascade.

TABLE I

| Gene | Gene Product |
| --- | --- |
| ninaA | Peptidyl-prolyl cis-trans isomerase |
| ninaB | β,β-carotene-15,15'-dioxygenase |
| ninaC | Single-headed myosin and protein kinase |
| ninaD | Retinal biosynthetic enzyme |
| ninaE | Opsin (blue) |
| Rh2 | Opsin (violet) |
| Rh3 | Opsin (ultraviolet) |
| Rh4 | Opsin (ultraviolet) |
| Rh5 | Opsin (blue) |
| Rh6 | Opsin (green) |
| arrestin-1 | Retinal photocycle |
| arrestin-2 | Retinal photocycle |
| Gqα | Heterotrimeric G protein _ subunit |
| Gqβ | Heterotrimeric G protein _ subunit |
| Gqγ | Heterotrimeric G protein _ subunit |
| inaC | Protein kinase C |
| inaD | Multivalent PDZ-domain protein |
| norpA | Phospholipase C |
| rdgA | Diacylglycerol kinase |
| rdgB | Phosphatidylinositol transfer protein |
| rdgC | Rhodopsin phosphatase |
| trp | "Light-activated" cation channel |
| trpl | "Light-activated" cation channel |

The present invention demonstrates that, of the gene products in Table I, the combination of (i) at least one opsin gene product from the six opsin gene products identified, (ii) at least one arrestin gene product from the two arrestin gene products identified, and (iii) $G_q\alpha$ is sufficient to cause a non-photoreceptor cell to undergo an increase in intracellular second messenger molecules, such as $IP_3$ and $Ca^{2+}$, followed by membrane depolarization when photostimulated with light of an appropriate wavelength (provided that the cell is also provided with retinal or a suitable derivative thereof). Notwithstanding the above, other gene products, either from Table I or otherwise, could additionally be provided to a non-photoreceptor cell undergoing photosensitization as described above. ChARGe emerged from experiments that measured photocurrents elicited in Xenopus oocytes by combinations of 10 candidate proteins derived from Drosophila photoreceptors (FIG. 1). The 10 candidate proteins included NinaE; NinaA, a peptidyl-prolyl cis-trans isomerase implicated in folding and intracellular transport of NinaE (Shieh, Stamnes et al. "The ninaA gene required for visual transduction in Drosophila encodes a homologue of cyclosporin A-binding protein," Nature 67–70 (1989)); arrestin-2 (Hyde, Mecklenburg et al. "Twenty Drosophila visual system cDNA clones: one is a homolog of human arrestin," Proc Natl Acad Sci USA 1008–12 (1990); LeVine, Smith et al. "Isolation of a novel visual-system-specific arrestin: an in vivo substrate for light-dependent phosphorylation," Mech Dev 19–25. (1990); Yamada, Takeuchi et al. "A 49-kilodalton phosphoprotein in the Drosophila photoreceptor is an arrestin homolog," Science 483–6 (1990)); the α, β, and γ subunits of the cognate heterotrimeric G-protein (Lee, Dobbs et al. "dgq: a drosophila gene encoding a visual system-specific G alpha molecule," Neuron 889–98. (1990); Yarfitz, Niemi et al. "A Gβ protein in the Drosophila compound eye is different from that in the brain," Neuron 429–38. (1991); Schulz, Huber et al. "A novel Gγ isolated from Drosophila constitutes a visual G protein γ subunit of the fly compound eye," J Biol Chem 37605–10 (1999)); NorpA, an eye-specific PLC (Bloomquist, Shortridge et al. "Isolation of a putative phospholipase C gene of Drosophila, norpA, and its role in phototransduction," Cell 723–33 (1988)); the "light-activated" cation channels transient receptor potential and TRPL (Montell and Rubin "Molecular characterization of the Drosophila trp locus: a putative integral membrane protein required for phototransduction," Neuron 1313–23 (1989); Hardie and Minke "The trp gene is essential for a light-activated Ca2+ channel in Drosophila photoreceptors," Neuron 643–51 (1992); Phillips, Bull et al. "Identification of a Drosophila gene encoding a calmodulin-binding protein with homology to the trp phototransduction gene," Neuron 631–42 (1992)); and InaD, a multivalent adaptor thought to collect transduction components into discrete signaling units (Shieh and Niemeyer "A novel protein encoded by the InaD gene regulates recovery of visual transduction in Drosophila," Neuron 201–10 (1995); Huber, Sander et al. "Phosphorylation of the InaD gene product, a photoreceptor membrane protein required for recovery of visual excitation," J Biol Chem 11710–7 (1996); Tsunoda, Sierralta et al. "A multivalent PDZ-domain protein assembles signalling complexes in a G-protein-coupled cascade," Nature 243–9 (1997); Scott and Zuker "Assembly of the Drosophila phototransduction cascade into a signalling complex shapes elementary responses," Nature 805–8 (1998)). Of these, omission of NinaE, arrestin-2, and the G-protein α subunit abolished the photocurrent, proving that each of these components was essential for function and a legitimate member of chARGe. None of the remaining seven proteins, including the ion channels transient receptor potential and transient receptor potential-like, had any discernable effect (FIG. 1). This suggested that transient receptor potential and transient receptor potential-like channels, the carriers of the photocurrent in the photoreceptors of the fly, were inactive in the heterologous environment.

Figure 9:
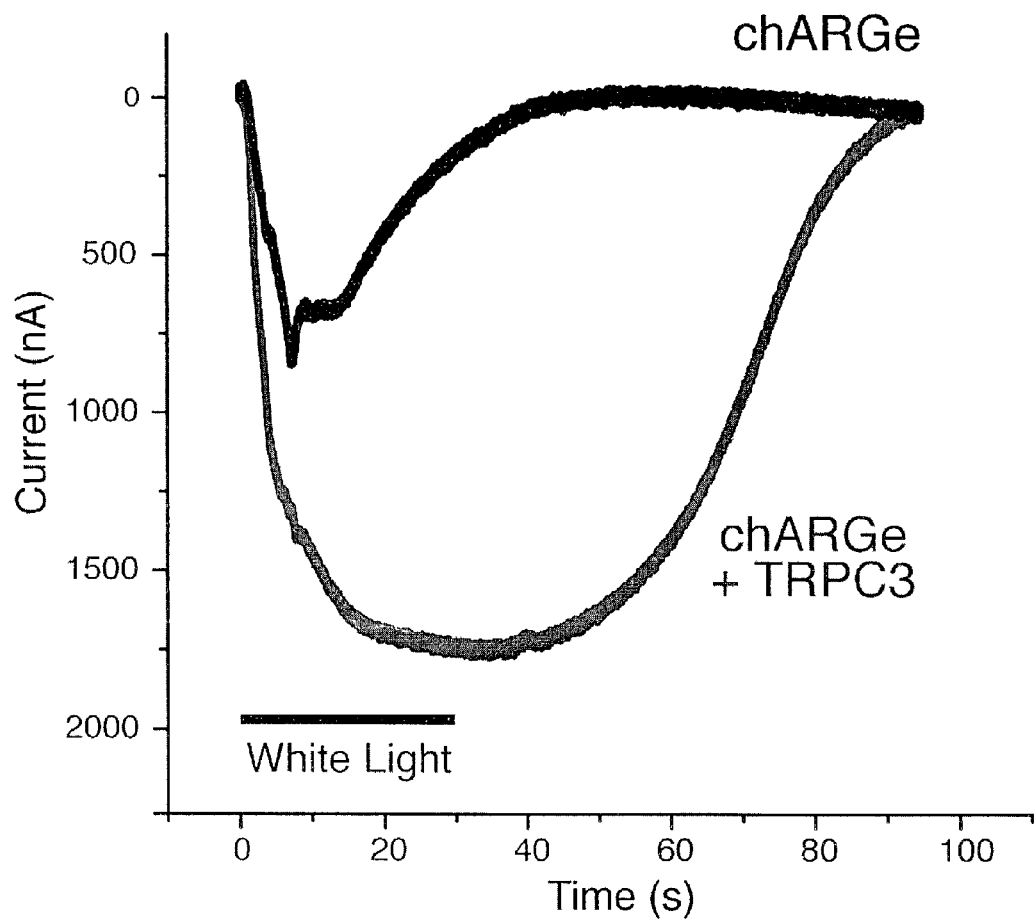
FIG. 9 shows the effect of TRPC3 of enhancing the photocurrent due to chARGe. Xenopus oocytes were programmed to express the minimal chARGe, consisting of NinaE, arrestin-2, and $G\alpha$; or the minimal chARGe plus TRPC3. Oocytes were exposed to 40 µM synthetic all-trans retinal for 15 min, membrane potentials were clamped to –80 mV and transmembrane currents recorded during periods of darkness and white illumination. Inward currents are displayed as downward deflections from baseline; the zero time point is defined as the onset of the light stimulus.

A person having ordinary skill in this art would readily recognize that additional gene products derived from the three main groups could be incorporated into in an improved version of chARGe:

The first group includes vertebrate ion channels gated by $IP_3$ and/or diacylglycerol, the small-molecule messengers produced by PLC. The principal diacylglycerol- and $IP_3$-gated channels in the plasma membrane of vertebrates are the members of the TRPC subfamily of the TRP superfamily of ion channels (Minke and Cook "TRP Channel Proteins and Signal Transduction," *Physiol Rev* 429–72. (2002; Montell, Birnbaumer et al. "The TRP Channels, a Remarkably Functional Family.," *Cell* 595–598 (2002)); as such, they are direct homologs of the fly photoreceptor channels. At least seven family members exist. At least one of them, TRPC3, is indeed able to boost the chARGe-triggered photocurrent in oocytes considerably (FIG. 9). TRPC3 is thought to be gated through a direct physical interaction of its cytoplasmically exposed C-terminus with the N-terminal ligand-binding domain of the $IP_3$ receptor, which itself is localized to the smooth endoplasmic reticulum (Mikoshiba "The InsP3 receptor and intracellular Ca2+ signaling," *Curr Opin Neurobiol* 339–45 (1997)). Because the isolated $IP_3$-binding domain of the receptor is able to bestow $IP_3$-dependent gating on TRPC3 (Kiselyov, Xu et al. "Functional interaction between InsP3 receptors and store-operated Htrp3 channels," *Nature* 478–82 (1998); Kiselyov, Mignery et al. "The N-terminal domain of the IP3 receptor gates store-operated hTrp3 channels," *Mol Cell* 423–9 (1999)), engineered channel constructs that carry this domain covalently fused to their N- or C-termini may provide additional enhancements. In addition, the isolated ligand-binding domain of the $IP_3$-receptor could be overexpressed in "trans", as a separate molecular entity anchored to the inner leaflet of the plasma membrane through a prenyl group attached to an engineered CAAX box. This arrangement is expected to facilitate encounters between the $IP_3$-binding domain and TRPC3.

The second group of envisioned modifications of chARGe includes adaptor or scaffolding proteins. In fly photoreceptors, the multivalent PDZ protein InaD serves as a clamp that assembles phototransduction components (rhodopsin, G protein, PLC, and TRP channels) into highly efficient signaling units that achieve single-photon sensitivity (Huber, Sander et al. "Phosphorylation of the InaD gene product, a photoreceptor membrane protein required for recovery of visual excitation," *J Biol Chem* 11710–7 (1996); Tsunoda, Sierralta et al. "A multivalent PDZ-domain protein assembles signalling complexes in a G-protein-coupled cascade," *Nature* 243–9 (1997); Scott and Zuker "Assembly of the *Drosophila* phototransduction cascade into a signalling complex shapes elementary responses," *Nature* 805–8 (1998); Montell "Visual transduction in *Drosophila*," *Annu Rev Cell Dev Biol* 231–68 (1999)). Either invertebrate TRP channels or vertebrate TRP homologs (e.g., TRPC3) could be localized to InaD complexes by transplanting the polypeptide segment recognized by InaD (Shieh and Zhu "Regulation of the TRP Ca2+ channel by INAD in *Drosophila* photoreceptors," *Neuron* 991–8 (1996)). Co-localization of receptor and effector should enhance sensitivity further.

The third group of additional chARGe constituents includes components that affect phosphoinositide and second messenger metabolism. Genetic evidence indicates that RdgA, a diacylglycerol kinase that converts diacylglycerol to phosphatidic acid, leads to constitutive activation of TRP channels (Raghu, Usher et al. "Constitutive activity of the light-sensitive channels TRP and TRPL in the *Drosophila* diacylglycerol kinase mutant, rdgA," *Neuron* 169–79 (2000)). Expression of RdgA along with the core chARGe components could achieve tighter temporal control over photoactivation.

A person having ordinary skill in this art would readily recognize that the arrestin gene products identified above may be truncated at their respective C-termini to bind more tightly to rhodopsin. Such tight binding may also help to shut down the phototransduction cycle when the light stimulus is removed.

Although the present invention has been described in the context of the *Drosophila* phototransduction cascade, the aforementioned *Drosophila* opsin gene product, arrestin gene product and/or $G_q\alpha$ could be replaced with analogous phototransduction gene products found in a number of invertebrates including, but not limited to, honey bee, squid, octopus, shrimp, scallop, sea slug and horseshoe crab.

In accordance with the teachings of the present invention, the manner in which an opsin gene product, an arrestin gene product and $G_q\alpha$ are provided to a cell is by introducing into the cell the nucleic acid sequences encoding the subject proteins, each nucleic acid sequence being operatively linked to a corresponding promoter that is active in the cell, and then allowing the cell to co-express the sequences to yield the proteins. The introduction of the nucleic acid sequences into the non-photoreceptor cell may be achieved by incorporating the sequences into one or more plasmids, which are then taken up by the non-photoreceptor cell by transfection. Alternatively, the sequences may be incorporated into one or more viral vectors, which are then used to infect the non-photoreceptor cell, or the sequences may be microinjected into the non-photoreceptor cell. As can readily be appreciated, by introducing the sequences into a fertilized oocyte, one could create a transgenic animal (see U.S. Pat. No. 4,736,866) wherein the sequences are incorporated into the genome of the animal and, therefore, are present in each cell of that animal's offspring.

The nucleic acid sequence data for at least one opsin gene, at least one arrestin gene and the $G_q\alpha$ subunit gene are known (see GenBank accession number K02315 for the opsin gene ninaE, GenBank accession number M32141 for the arrestin gene Arrestin-2, and GenBank accession number M58016 for the $G_q$ protein alpha subunit gene dgq; see also Provencio et al., "Melanopsin: An opsin in melanophores, brain, and eye," *Proc. Natl. Acad. Sci. USA*, 95:340–5 (1998); Pepe, "Rhodopsin and phototransduction," *J. Photochem. Photobiol. B: Biol.*, 48:1–10 (1999); and Hargrave, "Rhodopsin Structure, Function, and Topography," *IOVS*, 42(1):3–9 (January 2001)). Accordingly, nucleic acid sequences for the subject genes can be constructed using conventional nucleic acid synthesis techniques. Alternatively, the aforementioned nucleic acid sequence data can be used to synthesize partial-length nucleic acid oligomers which can then be used to isolate the corresponding full-length sequences from the *Drosophila* genome using conventional isolation and amplification techniques.

Where the introduction of the subject nucleic acid sequences has not been restricted to a particular cell or to a particular cell type, but rather, has the potential of having been introduced into two or more different cell types within a heterogenous population of cells, it may be desirable to express the nucleic acid sequences only when they are present in a desired cell type so as to render only that cell type sensitive to photostimulation. This may be desirable, for example, where one wishes to identify the neuronal pathway of only a particular species of neuron within the brain. Such selective expression may be achieved, for example, by operatively coupling the subject nucleic acid sequences to promoters (which may be the same or different) that are active only when present in the targeted cell type.

Examples of cell specific promoters include the following: the promoter for GABA decarboxylase (Makinae, Kobayashi et al. "Structure of the mouse glutamate decarboxylase 65 gene and its promoter: preferential expression of its promoter in the GABAergic neurons of transgenic mice," *J Neurochem* 1429–37. (2000)), which is specific for inhibitory neurons; the promoter/enhancer for Wnt-1 and the endothelin receptor B promoter (Zinyk, Mercer et al. "Fate mapping of the mouse midbrain-hindbrain constriction using a site-specific recombination system," *Curr Biol* 665–8. (1998); Jiang, Rowitch et al. "Fate of the mammalian cardiac neural crest," *Development* 1607–16. (2000)), both of which are specific for the mouse neural crest; vesicular glutamate promoter (Takamori, Rhee et al. "Identification of differentiation-associated brain-specific phosphate transporter as a second vesicular glutamate transporter (VGLUT2)," *J Neurosci* RC182. (2001)); calbindin promoter specific for the Purkinje cells of the cerebellum (Arnold and Heintz "A calcium responsive element that regulates expression of two calcium binding proteins in Purkinje cells," *Proc Natl Acad Sci USA* 8842–7. (1997)); a 2 kb promoter for synaptic vesicle protein synapsin 1, which has been used to express transgenes in neuroblastoma and other neuronal cell lines, but not in non-neuronal cell lines (Kugler, Meyn et al. "Neuron-specific expression of therapeutic proteins: evaluation of different cellular promoters in recombinant adenoviral vectors," *Mol Cell Neurosci* 78–96. (2001)); platelet-derived growth factor B-chain (PDGF B) promoter, which has been used to preferentially target neurons in the cortex, cerebellum and hippocampus (Georgopoulos, McKee et al. "Generation and characterization of two transgenic mouse lines expressing human ApoE2 in neurons and glial cells," *Biochemistry* 9293–301. (2002); Rockenstein, Mallory et al. "Differential neuropathological alterations in transgenic mice expressing alpha-synuclein from the platelet-derived growth factor and Thy-1 promoters," *J Neurosci Res* 568–78. (2002)); a 1.8 kb neuron-specific enolase (NSE) promoter, which has been used to express transgenes in mouse retina and spinal cord (Sakai, Thome et al. "Inducible and brain region-specific CREB transgenic mice," *Mol Pharmacol* 1453–64. (2002)); 2.9 kb of upstream non-coding DNA from the myosin heavy chain gene (MHC promoter/enhance), which has been used to direct transgene expression in the mouse heart (Matsui, Li et al. "Phenotypic spectrum caused by transgenic overexpression of activated Akt in the heart," *J Biol Chem* 22896–901. (2002)); 1.6 kb of retinoblastoma gene (RB) promoter, which has been used to label eye ganglion layer, neurons of the cerebellum, glial cells of the thalamus and myocytes in the thigh muscle (Jiang, Guo et al. "Retinoblastoma gene promoter directs transgene expression exclusively to the nervous system," *J Biol Chem* 593–600. (2001)); 0.9 kb of whey acidic protein (WAP) promoter, which has been used to target mammary epithelial cells (Ozturk-Winder, Renner et al. "The murine whey acidic protein promoter directs expression to human mammary tumors after retroviral transduction," *Cancer Gene Ther* 421–31. (2002)); 8.5 kb of $Ca^{2+}$-calmodulin-dependent protein kinase II subunit (CaMKII) promoter, which has been used to express transgenes in the mouse hippocampus, cortex, cerebellum and olfactory bulb (Jerecic, Schulze et al. "Impaired NMDA receptor function in mouse olfactory bulb neurons by tetracycline-sensitive NR1 (N598R) expression," *Brain Res Mol Brain Res* 96–104. (2001)); glucagon (Gcg) promoter, which has been used to express human growth hormone in the pancreatic islets (Yamaoka, Yoshino et al. "Transgenic expression of FGF8 and FGF10 induces transdifferentiation of pancreatic islet cells into hepatocytes and exocrine cells," *Biochem Biophys Res Commun* 138–43. (2002)); insulin (Ins2) promoter, which has been used to express human growth hormone in the β-cell of the pancreas (Herrera "Adult insulin- and glucagon-producing cells differentiate from two independent cell lineages," *Development* 2317–22. (2000)); Myh6 promoter, which is specific for mouse heart cells (Lee, Morley et al. "Conditional lineage ablation to model human diseases," *Proc Natl Acad Sci USA* 11371–6. (1998)); Lap promoter, which is specific for mouse liver cells (Lavon, Goldberg et al. "High susceptibility to bacterial infection, but no liver dysfunction, in mice compromised for hepatocyte NF-kappaB activation," *Nat Med* 573–7. (2000)); and Fabp promoter, which is specific for mouse small intestine cells (Saam and Gordon "Inducible gene knockouts in the small intestinal and colonic epithelium," *J Biol Chem* 38071–82. (1999)).

Additional promoters, as well as techniques for identifying promoters specific for particular cell types and/or two-component gene expression systems (involving, for example, transcriptional transactivation or site-specific DNA recombination) are disclosed in DeFalco et al., "Virus-Assisted Mapping of Neural Inputs to a Feeding Center in the Hypothalamus," *Science,* 291:2608–13 (Mar. 30, 2001); Zemelman et al., "Genetic schemes and schemata in neurophysiology," *Current Opinion in Neurobiology,* 11:409–14 (2001); Sandberg et al., "Regional and strain-specific gene expression mapping in the adult mouse brain," *PNAS,* 97(20):11038–11043 (Sep. 26, 2000); Lewandoski, "Conditional Control of Gene Expression in the Mouse," *Nature Reviews/Genetics,* 2:743–55 (October 2001); and Stanford et al., "Gene-Trap Mutagenesis: Past, Present and Beyond," *Nature Reviews/Genetics,* 2:756–68 (October 2001).

One possible way to confine chARGe gene expression to a specific targeted cell type is by the inclusion of a cassette in the chARGe gene expression vector that contains any or all of the following: an mRNA splice donor site, translation stop codons, or a transcription termination sequence. Such a "stop cassette" may be under control of Cre recombinase via the inclusion of loxP bacteriophage P1 Cre recombinase target sequences upstream and downstream of the stop cassette (Ray, Fagan et al. "The Cre-loxP system: a versatile tool for targeting genes in a cell- and stage-specific manner," *Cell Transplant* 805–15. (2000); Lewandoski "Conditional Control of Gene Expression in the Mouse," *Nature Review Genetics* 743–755 (2001); Metzger and Chambon "Site- and time-specific gene targeting in the mouse," *Methods* 71–80. (2001)). The chARGe genes will only be expressed when Cre recombinase is present to remove the stop cassette, thereby limiting ChARGE gene expression to cells where Cre recombinase is present. A possible way to target specific cells in an animal for chARGe gene expression includes the use of a virus with a stop cassette to infect Cre-expressing tissues of an animal. Alternatively, a transgenic animal containing the stop cassette as well as the silent transgenes in all cells can be mated with an animal expressing Cre recombinase in specific cells to generate transgenically active progeny.

Cell type-specific ChARGE gene expression may be accomplished in *Drosophila melanogaster* by the use of transgenic strains carrying promoters that drive expression of chARGe genes in particular tissues. Such promoters may include OR83b (an olfactory receptor gene that is expressed in approximately 70% of the population of olfactory receptor neurons) (Vosshall, Wong et al. "An olfactory sensory map in the fly brain," *Cell* 147–59 (2000)), the glutamic acid decarboxlyase promoter Gad1 (the gene encoding the key enzyme in GABA biosynthesis, that is expressed in GABAergic inhibitory local neurons), and GH146 (a regulatory sequence that drives expression in projection neurons) (Stocker, Heimbeck et al. "Neuroblast ablation in *Drosophila* P[GAL4] lines reveals origins of olfactory interneurons," *J Neurobiol* 443–56 (1997)).

On the other hand, there may be situations in which it is desirable to have gene expression occur in virtually any type of cell into which the genes are introduced, as opposed to being limited to particular cell types. In such instances, the genes are operatively coupled to non-specific promoters, such as the Ubiquitin promoter or the SV40 promoter or the CMV promoter.

Because several of the opsin gene products identified above have distinctive absorption maxima, one could operatively couple different opsin genes to different promoters specific for particular cell types and, in this manner, render different cell types sensitive to photostimulation with different wavelengths of light. This could be used, for example, to identify a number of different neuronal pathways within a single brain sample. To provide an even greater variety of opsin gene products, one could design opsin gene product variants that have absorption maxima distinguishable from those of the above-listed opsin gene products. In addition, one could design opsin gene products that optimize subcellular targeting, that eliminate regulatory sites involved in light adaptation (see Vinos et al., "A G protein-coupled receptor phosphatase required for rhodopsin function," *Science*, 277:687–90 (1997)) and/or that minimize the triggering of an immune response in a target organism (e.g., by replacing the first 39 amino acid residues of the *Drosophila* opsin with those from human rhodopsin).

In addition to the three gene products identified above, the methods of the present invention require the use of retinal or a suitable derivative thereof to generate the active photopigment rhodopsin from unliganded opsin. The retinal, either the 11-cis or the all-trans isomer, can be supplied either exogenously (as is the case for in vitro applications) or endogenously (as may be the case for in vivo applications). Both retinal (which is used in vertebrate photoreceptor cells) and 3-hydroxyretinal (which is used in invertebrate photoreceptor cells) are functional with *Drosophila* opsin gene products. In vertebrates, all-trans retinal is synthesized from all-trans retinol (vitamin A) in a single enzymatic reaction catalyzed by a family of widely expressed alcohol and short-chain dehydrogenases. Accordingly, one could provide the necessary retinal to a non-photoreceptor cell by supplying retinol in the presence of a suitable dehydrogenase and having the retinol bio-converted to retinal.

As explained above, the sensitization of a non-photoreceptor cell to light using the technique of the present invention results, when photostimulation is applied, in an intracellular increase of second messengers, including $IP_3$ and/or calcium ions. Depending upon the type of non-photoreceptor cell sensitized, the secondary effects of an increase in intracellular calcium ion concentration may include, but are not limited to, the release of neurotransmitters and opiates from nerve cells, the secretion of histamine by mast cells, the release of serotonin by blood platelets, glycogenolysis in liver cells, insulin secretion by pancreatic islet cells, epinephrine secretion by adrenal chromaffin cells, T-cell and natural killer cell activation, smooth muscle contraction, transduction of taste by taste buds, and programmed cell death.

Also, by coupling photoactivation of rhodopsin to a G-protein alpha subunit other than the alpha subunit of $G_q$, one can elicit, through photostimulation, a response other than an increase in intracellular $IP_3$, $Ca^{2+}$, and DAG. For example, one could couple rhodopsin to the alpha subunit of $G_s$ or $G_i$ instead of $G_q$. See Hamm et al., "Heterotrimeric G Proteins," *Curr. Opin. Cell. Biol.*, 8:189–96 (1996); and Neer, "Heterotrimeric G Proteins: Organizers of Transmembrane Signals," *Cell*, 80:249–57 (1995).

$G_s$ activates adenylate cyclase (AC), which converts ATP to cAMP. cAMP, like $IP_3$ and DAG, is a cellular messenger that profoundly affects the biochemistry of those cells in which it is generated. cAMP plays a critical role in the formation of short-term and long-term memories, increases acid secretion from cells lining the stomach, speeds up the breakdown of stored nutrients in the liver, diminishes aggregation of blood platelets, regulates bronchial constriction, reabsorption of water in the kidney, and is involved in the perception of certain tastes. See Gilbertson et al., "The molecular physiology of taste transduction," *Current Opinion in Neurobiology*, 10:519–27 (2000). In addition, the effect of many hormones is mediated by cAMP, including but not limited to calcitonin, chorionic gonadotropin, corticotropin, epinephrine, follicle-stimulating hormone, glucagon, luteinizing hormone, lipotropin, melanocyte-stimulating hormone, norepinephrine, parathyroid hormone, serotonin, thyroid-stimulating hormone and vasopressin.

$G_i$ counteracts the effect of $G_s$ by inactivating adenylate cyclase. Transducin, a $G_i$ protein and a key player in vertebrate phototransduction, also activates cGMP phosphodiesterase, thereby lowering the levels of cGMP and closing ion channels in retinal rod cells (channel closing signaling that the photoreceptors have been exposed to light). In addition, $G_i$ proteins participating in the transduction of taste activate cAMP phosphodiesterase, thereby reducing the intracellular levels of cAMP in taste buds. Moreover, some $G_i$ proteins can open ion channels directly by binding to them. The effect of acetylcholine on an inward-rectifying potassium channel is mediated by $G_i$; see Mark et al., "G-protein mediated gating of inward-rectifier $K^+$ channels," *Eur. J. Biochem.*, 267:5830–6 (2000).

To couple the pathways controlled by the various G-protein subunits to rhodopsin activation, the alpha subunit of $G_q$ may be replaced with a chimeric subunit of a G protein. Examples of chimeric G protein subunits are described in Milligan et al., "Chimaeric G proteins: their potential use in drug discovery," *Trends Pharmacol. Sci.*, 20:118–24 (1999); Ostrom et al., "Stoichiometry and compartmentation in G protein-coupled receptor signaling: implications for therapeutic interventions involving G(s)," *J. Pharmacol. Exp. Ther.*, 294:407–12 (2000); and Coward et al., "Chimeric G Proteins Allow a High-Throughput Signaling Assay of $G_i$-Coupled Receptors," *Analytical Biochemistry*, 270:242–8 (1999). It has been found that the last 5 amino acids of a G-protein subtype are primarily responsible for specifying the receptor that will activate that protein. For example, a $G_q$ in which the last 5 amino acids have been replaced with those from a $G_s$ can couple the binding of acetylcholine to its receptor to calcium release and not to an increase in intracellular cAMP. See Conklin et al., "Carboxyl-terminal mutations of Gq alpha and Gs alpha that alter the fidelity of receptor activation," *Mol. Pharmacol.*, 50:885–90 (1996). In addition, $G_s$ bearing the terminal 5 amino acids of $G_q$ can be activated by rhodopsin. See Natochin et al., "Probing the mechanism of rhodoposin-catalyzed transducin activation," *J. Neurochem.*, 77:202–10 (2001); and Natochin et al., "Rhodopsin recognition by mutant G(s)alpha containing C-terminal residues of transducin," *J. Biol. Chem.* 275: 2669–75 (2000). Receptor specificity of G-proteins can be more precisely tuned by swapping additional amino acid residues between the 4 and 5 G-protein helices. See Kostenis et al., "Genetic analysis of receptor-G alpha q coupling selectivity," *J. Biol. Chem.*, 272:23675–81 (1997).

Another alternative to using the above-described *Drosophila* protein trio of opsin/arrestin/$G_q\alpha$ to photosensitize a non-photoreceptor cell involves using melanopsin, a dermal opsin found in frogs (McClintock, Rising et al. "Melanophore pigment dispersion responses to agonists show two patterns of sensitivity to inhibitors of cAMP-dependent protein kinase and protein kinase C," *J Cell Physiol* 1–7. (1996); Provencio, Jiang et al. "Melanopsin: An opsin in melanophores, brain, and eye," *Proc Natl Acad Sci USA* 340–5. (1998)), and its respective G-protein alpha subunit $G_s$. Melanopsin activates $G_s$ which, in turn, activates the AC second messenger pathway.

Still another alternative to using the aforementioned *Drosophila* trio involves making use of the photostimulation pathway employed in the parietal eyes of lizards (Finn, Solessio et al. "A cGMP-gated cation channel in depolarizing photoreceptors of the lizard parietal eye," *Nature* 815–9 (1997)). Photoreceptors in the parietal eyes of lizards, like vertebrate retinal photoreceptors, use cGMP to signal light stimulation. However, in the lizard parietal cells, the concentration of cGMP rises in response to light and the photoreceptors depolarize. Since the cGMP-gated channel in the parietal photoreceptors is very similar to its rod cell counterpart, the parietal cell pathway offers another vertebrate alternative to the above-discussed *Drosophila* trio.

In yet another alternative to using the aforementioned *Drosophila* trio involves making use of mammalian taste transduction (Kolesnikov and Margolskee "A cyclic-nucleotide-suppressible conductance activated by transducin in taste cells," *Nature* 85–8. (1995); Ruiz-Avila, McLaughlin et al. "Coupling of bitter receptor to phosphodiesterase through transducin in taste receptor cells," *Nature* 80–5. (1995); Gilbertson, Damak et al. "The molecular physiology of taste transduction," *Curr Opin Neurobiol* 519–27. (2000)). One pathway involved in mammalian taste transduction uses transducin, the same G-protein found in retinal rods, to activate a phosphodiesterase and lower the level of cAMP in response to bitter taste. However, unlike the channels in photoreceptor cells, the taste bud channels open when cAMP levels decrease, causing the cells to depolarize. Therefore, one should be able to stimulate non-photoreceptor neurons to fire in response to light by expressing the mammalian counterparts to the *Drosophila* trio, along with the channel from taste receptor cells. In the absence of the channel, this pathway can be used to lower intracellular cAMP levels, thereby countering the effects of many of the hormones discussed above. Another pathway involved in mammalian taste transduction uses gustducin, a G protein very similar to retinal transducin. Like *Drosophila* $G_q\alpha$, gustducin activates PLC, producing $IP_3$ and diacylglycerol. Consequently, a chimeric gustducin that is capable of interacting with rhodopsin could replace the *Drosophila* $G_q\alpha$ protein.

To detect a neuronal pathway within a neural tissue sample using the methods of the present invention, the genes encoding the opsin, arrestin and $G_q\alpha$ gene products are first introduced into the cell population, each preferably under the control of a promoter specific for a targeted cell type. The genes are then expressed in the targeted cells of the sample, and retinal or a derivative thereof is provided to the cells so that rhodopsin may be formed. The locations of neurons making functional synaptic connections to a neuron of interest are then revealed by monitoring the neurons of interest while irradiating other neurons in the sample.

One of the advantages of the present methods over existing methods of detecting neuronal pathways is that one need not confine the illumination to a single cell to avoid an indiscriminate response. Instead, one can illuminate a comparatively large area of the sample and still confine stimulation to a single cell since only the targeted cells have been rendered genetically sensitive to photostimulation. In effect, the present method localizes the response, rather than the stimulus. Moreover, because the cells being tested can be targeted based on their genetic makeup, as opposed to their physical characteristics, one can test the targeted cells without knowing, a priori, where they are located within the sample. Furthermore, because three of the four essential components of the present technique are encoded genetically and the fourth can be generated biosynthetically from vitamin A, once the gene transfer step has been accomplished (where a transgenic animal is not involved), no exogenous chemicals need to be added and no pharmacokinetic barriers need to be overcome.

In addition to being used to detect neuronal pathways, another application of the photosensitizing techniques of the present invention involves rendering pancreatic islet cells sensitive to photostimulation. Such cells could then, for example, be implanted in a diabetic patient and optically coupled to a light source so that, when blood sugar levels are detected by a sensor to drop too low, the light source is turned on, thereby causing the pancreatic islet cells to be photostimulated to secrete insulin. Instead of having activation of the light source coupled to a blood sugar measurement by the sensor, activation of the light source could be manually controlled by the patient who could, for example, activate the light source soon after ingesting a meal.

Yet another application of the photosensitizing technique of the present invention involves rendering natural opiate-producing nerve cells sensitive to photostimulation. In the patient such cells could be infected by a viral vector containing the phototransduction genes mentioned above and the cells could be optically coupled to a light source manually controllable by the patient. In this manner, when the patient desires pain relief, the light source is turned on, thereby causing the photostimulated cells to secrete the endogenous opiate. Such a treatment for pain is expected to be far less addictive than currently prescribed painkillers.

Yet another application of the photosensitizing technique of the present invention involves rendering cells in the brain that respond to the levels of leptin in the bloodstream sensitive to photostimulation. Leptin is a protein normally produced by adipose tissue, and these brain cells can adjust the metabolic rate and the sensation of hunger depending on the leptin levels encountered. These brain cells can be infected with a virus carrying the genes necessary for rendering them sensitive to photostimulation. Promoters specific for these cells will ensure that the photostimulation proteins will not be expressed in any other brain cells. Illuminating these cells with the proper amount of light will then offer individuals wishing to change their weight a way to control their hunger and metabolic rate.

Still another application of the photosensitizing technique of the present invention is in a method of treating brain cancer, said method comprising infecting brain cells with a virus carrying the genes necessary for rendering a cell sensitive to photostimulation. Because cancerous brain cells divide and non-cancerous brain cells do not, only the cancerous brain cells will receive and, therefore, express the subject genes. By then irradiating the cancerous brain cells with a sufficient amount of light, one can raise the intracellular concentration of $Ca^{2+}$ in the cancerous cells to toxic levels, thereby resulting in their death.

In yet another application of the photosensitizing technique of the present invention, there is provided a method of treating incontinence. This method comprises transforming those muscle cells involved in bladder control so that they are rendered sensitive to photostimulation. These muscle cells could then be coupled to a light source and strengthened through a regimen of photostimulation.

In yet another application of the photosensitizing technique of the present invention, there is provided a method for treating Parkinson's Disease. This method comprises transforming those neuronal cells implicated in muscle tremors, so that they are rendered sensitive to photostimulation. These neuronal cells could then be coupled to a light source and their firing controlled through a regimen of photostimulation (Carbon and Eidelberg "Modulation of regional brain function by deep brain stimulation: studies with positron emission tomography," *Curr Opin Neurol* 451–5. (2002); Kiss, Mooney et al. "Neuronal response to local electrical stimulation in rat thalamus: physiological implications for mechanisms of deep brain stimulation," *Neuroscience* 137–43 (2002)).

In yet another application of the photosensitizing technique of the present invention, there is provided a method for treating depression and anxiety. This method comprises transforming those neuronal cells implicated in depression and anxiety so that they are rendered sensitive to photostimulation. These neuronal cells could then be coupled to a light source and activated through a regimen of photostimulation.

In yet another application of the photosensitizing technique of the present invention, there is provided a method for enhancing attention and memory. This method comprises transforming those neuronal cells implicated in attention and memory retention so that they are rendered sensitive to photostimulation. These neuronal cells could then be coupled to a light source and activated through a regimen of photostimulation.

In yet another application of the photosensitizing technique of the present invention, there is provided a method for treating the lack of sexual arousal. This method comprises transforming those neuronal cells implicated in arousal so that they are rendered sensitive to photostimulation. These neuronal cells could then be coupled to a light source and activated through a regimen of photostimulation.

In yet another application of the photosensitizing technique of the present invention, there is provided a method for treating disorders of sleep. This method comprises transforming those neuronal cells implicated in regulation of sleep, so that they are rendered sensitive to photostimulation. These neuronal cells could then be coupled to a light source and activated through a regimen of photostimulation.

A person having ordinary skill in this art would recognize that one need not necessarily monitor or measure electrical activity exclusively in neighboring cells after stimulating chARGed cells. One may, for example, use genetically encodable optical sensors of neuronal activity (see Zemelman et al., "Genetic schemes and schemata in neurophysiology," *Current Opinion in Neurobiology*, 11:409–14 (2001)). One such sensor is called synapto-pHluorin (see Miesenböck, et al., *Nature* 1998 394:192–5). Synapto-pHluorins are pH-sensitive mutants of green fluorescent protein ('pHluorins'), developed by structure-directed combinatorial mutagenesis, linked to the lumenal end of a vesicle membrane protein VAMP, placing them inside synaptic vesicles before neurotransmitter is released and outside the cell after vesicle degranulation and neurotransmitter release. In the low pH of the vesicle, the Phluorins do not fluoresce. However, after the vesicle fuses with the plasma membrane, pHluorins end up in the neutral extracellular medium, where they start to fluoresce. Using various promoters one can put the photostimulation components into one set of cells and the pHluorins into another set. This way one can combine the two technologies either to see all of the neuronal consequences of photostimulation or to identify neuronal targets for photostimulation by monitoring the neuronal activity, after a natural stimulus has been applied, of an animal whose brain cells express an optical sensor and pinpointing the neurons activated by that stimulus.

The following examples are provided for illustrative purposes only and are in no way intended to limit the scope of the present invention:

EXAMPLE 1

Phototransduction Components

The coding regions (GenBank accession numbers in parentheses) of ninaE (K02315), ninaA (M62398), arrestin-2 (M32141), Gα (dgq; M58016), Gβ (gbe; M76593), Gγ (AJ250440), norpA (J03138), trp (M34394), trpl (M88185) and inaD (U15803) were amplified by PCR from the *Drosophila* head cDNA library GH (Berkeley *Drosophila* Genome Project) and ligated to pXES43, a derivative of pGEMHE (Liman, Tytgat et al. "Subunit stoichiometry of a mammalian K+ channel determined by construction of multimeric cDNAs," *Neuron* 861–71 (1992)). Capped transcripts for injection into *Xenopus* oocytes were synthesized directly from these templates after linearization (MEGAscript T7, Ambion). Plasmids for expression in neurons (pChARGe-1 and pChARGe-2) were based on the pCI-neo backbone (Promega). pChARGe-1 carried ninaE and Gα under CMV- and SV40-control, respectively; pChARGe-2 contained sequences encoding EGFP (with a 20-amino acid N-terminal GAP-43 tag that confers plasma membrane association [Moriyoshi et al., 1996]) and arrestin-2 in the equivalent expression cassettes.

Synthetic all-trans retinal (Sigma) was diluted, from a 100-mM stock in DMSO, to 40 μM in the appropriate extracellular recording solution (see below) and allowed to bind to NinaE for 15 min in the dark. A mechanically shuttered (Uniblitz, Vincent Associates) Lambda DG-4 rapid wavelength changer (Sutter Instruments) delivered <2 mW of stimulating light without ultraviolet and infrared (E400LP, Chroma; Hot Mirror, Newport) components through 20×/0.4 (oocytes) or 40×/0.8 W (neurons) Zeiss Achroplan objectives. In some experiments, a short pre-illumination with red light (E600LP plus HQ625/40, both from Chroma) preceded the white-light stimulus. Light source and shutter were controlled through pClamp 8.0 (Axon Instruments) and MetaFluor 4.5 (Universal Imaging).

EXAMPLE 2

*Xenopus* Oocytes

Stage VI oocytes were microinjected with the specified mRNA mixtures, which were adjusted to keep the doses of individual messages constant at 2–4 fmol/oocyte. Photocurrents were recorded at −80 mV with a two-electrode voltage-clamp amplifier (Axoclamp-2B, Axon Instruments) 2–4 days after mRNA injection. Electrodes (2–3 MΩ) were filled with 3 M KCl; the extracellular recording solution (Barth's Saline) contained, in mM, 87.5 NaCl, 2 KCl, 2.4 NaHCO$_3$, 2 CaCl$_2$, 1 MgCl$_2$, 5 Tris-HCl, pH 7.2. Signals were externally amplified (CyberAmp 380, Axon Instruments) before digitization at 100 Hz (Digidata 1200, Axon Instruments). To block IP$_3$-sensitive Ca$^{2+}$ stores where indicated, 20 µM xestospongin C (Gafni et al., 1997; Calbiochem) was present throughout the experiment, beginning with the retinal load.

EXAMPLE 3

Rat Hippocampal Neurons

Figure 3:
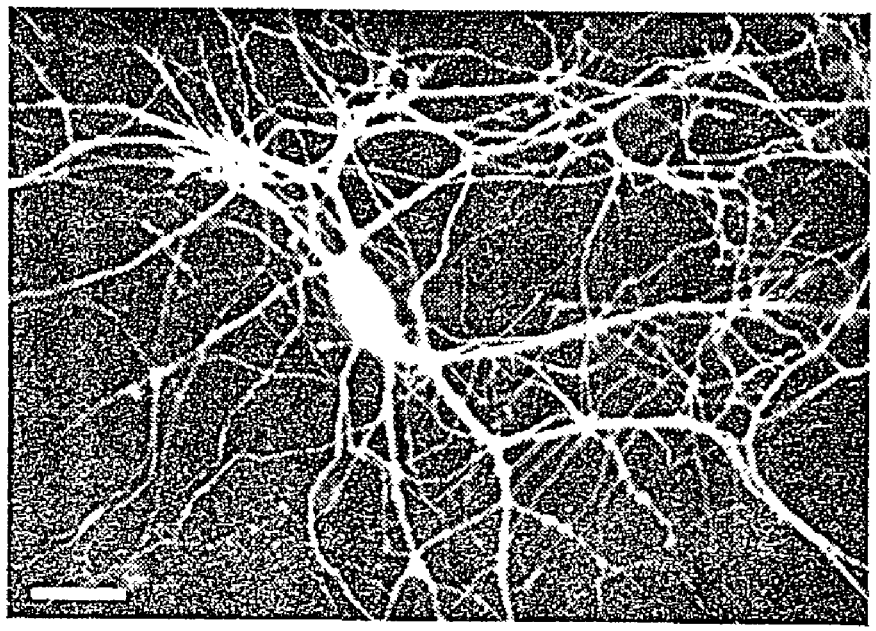
FIG. 3 shows the identification of a chARGed hippocampal neuron in primary culture. ChARGed neurons express a membrane-bound version of EGFP (Moriyoshi, Richards et al. "Labeling neural cells using adenoviral gene transfer of membrane-targeted GFP," *Neuron* 255–60. (1996)) that permits their identification during live microscopy. Scale bar, 20 µm.

Hippocampal neurons obtained from E19 rats were grown in dissociated cultures (Yuste, Miller et al. "Synapto-pHluorins: chimeras between pH-sensitive mutants of green fluorescent protein and synaptic vesicle membrane proteins as reporters of neurotransmitter release," *Methods Enzymol* 522–46 (2000)) and transfected with a calcium phosphate precipitate (pH 7.08) formed from a 1:1 mixture of CsCl-banded pChARGe-1 and pChARGe-2. Neurons were exposed to 4.2 µg/cm$^2$ of precipitated DNA for 20 minutes. Transfections were done on day 8 after plating, recordings on days 6–10 after transfection. Neurons were identified under DIC and epifluorescence illumination (to distinguish transfected from untransfected cells; FIG. 3) and placed under whole-cell current clamp before reconstitution of NinaE with retinal. Patch pipettes (~2.5 MΩ) contained, in mM, 120 K-gluconate, 10 KCl, 5 ATP, 0.3 GTP, and 10 K-HEPES, pH 7.2. The extracellular recording solution contained, in mM, 119 NaCl, 2.5 KCl, 2 CaCl$_2$, 1 MgCl$_2$, 30 glucose, 25 Na-HEPES, pH 7.4. Membrane potentials were recorded with an Axoclamp-2B amplifier (Axon Instruments) in bridge mode and digitized at 5 kHz (Digidata 1200, Axon Instruments).

EXAMPLE 4

The Minimal "chARGe"

The simplicity of its retinal cycle should enable invertebrate phototransduction to function outside a specialized photoreceptor environment. Expressed ectopically, the invertebrate—but not the vertebrate—transduction machinery could serve as a light-controlled source of depolarizing current to stimulate electrical activity in excitable cells, or of intracellular Ca$^{2+}$ to activate Ca$^{2+}$-dependent processes such as neurotransmitter release. In a first test of this possibility, and in an effort to delineate the minimal set of transduction components necessary for sensitizing a non-photoreceptor cell to light, *Xenopus* oocytes were programmed with pools of mRNAs encoding combinations of 10 proteins with genetically or biochemically defined roles in *Drosophila* phototransduction, the most thoroughly characterized invertebrate system (Montell, 1999; Hardie and Raghu, 2001). The 10 candidate proteins included NinaE, the blue-sensitive opsin of R1–R6 photoreceptors (O'Tousa et al., 1985; Zuker et al., 1985); NinaA, a peptidyl-prolyl cis-trans isomerase implicated in folding and intracellular transport of NinaE (Shieh, Stamnes et al. "The ninaA gene required for visual transduction in *Drosophila* encodes a homologue of cyclosporin A-binding protein," *Nature* 67–70 (1989)); the major arrestin isoform, arrestin-2 (Hyde et al., 1990; LeVine et al., 1990; Yamada et al., 1990); the α, β, and γ subunits of the cognate heterotrimeric G-protein (Lee et al., 1990; Yarfitz et al., 1991; Schulz et al., 1999); NorpA, an eye-specific PLC (Bloomquist, Shortridge et al. "Isolation of a putative phospholipase C gene of *Drosophila*, norpA, and its role in phototransduction," *Cell* 723–33 (1988)); the "light-activated" cation channels TRP and TRPL (Montell and Rubin, 1989; Hardie and Minke, 1992; Phillips et al., 1992); and InaD, a multivalent adaptor thought to collect transduction components into discrete signalling units (Shieh and Niemeyer, 1995; Huber et al., 1996; Tsunoda et al., 1997; Scott and Zuker, 1998).

Unliganded NinaE in the membrane of voltage-clamped oocytes was reconstituted in the dark with 40 µM synthetic all-trans retinal, to form a metarhodopsin-like intermediate that could be further photoconverted (Hillman et al., 1983; Kiselev and Subramaniam, 1994; Ranganathan and Stevens, 1995) to rhodopsin. Since the reconstituted molecule incorporated a heterologous chromophore with unknown spectral properties—the retinal of vertebrates, which is available commercially, rather than the 3-hydroxyretinal of flies (Vogt and Kirschfeld "Chemical identity of the chromophores of fly visual pigment," *Naturwissenschaften* 211–3 (1984)), which is not—white light, expected to contain all spectral components necessary to drive the hybrid rhodopsin through its retinal cycle, was used as the stimulus.

Illumination of oocytes expressing the full complement of 10 photoreceptor proteins (expression of NinaE, arrestin-2, G_, NorpA, TRP, and InaD was confirmed by immunoblotting of oocyte extracts, results not shown; expression of NinaA, Gβ, Gγ, and TRPL was not tested) evoked positive currents with latencies to peak of 2.29 to 6.74 s and amplitudes of several hundred nA (n=15 oocytes) (FIG. 1A). Responses required reconstitution of NinaE with retinal (n=9 oocytes) (FIG. 1A) and were inhibited by 20 µM xestospongin C (n=5 oocytes), an antagonist of Ca$^{2+}$ release from IP$_3$-sensitive stores (Gafni, Munsch et al. "Xestospongins: potent membrane permeable blockers of the inositol 1,4,5-trisphosphate receptor," *Neuron* 723–33. (1997)) (FIG. 1A).

Figure 1B:
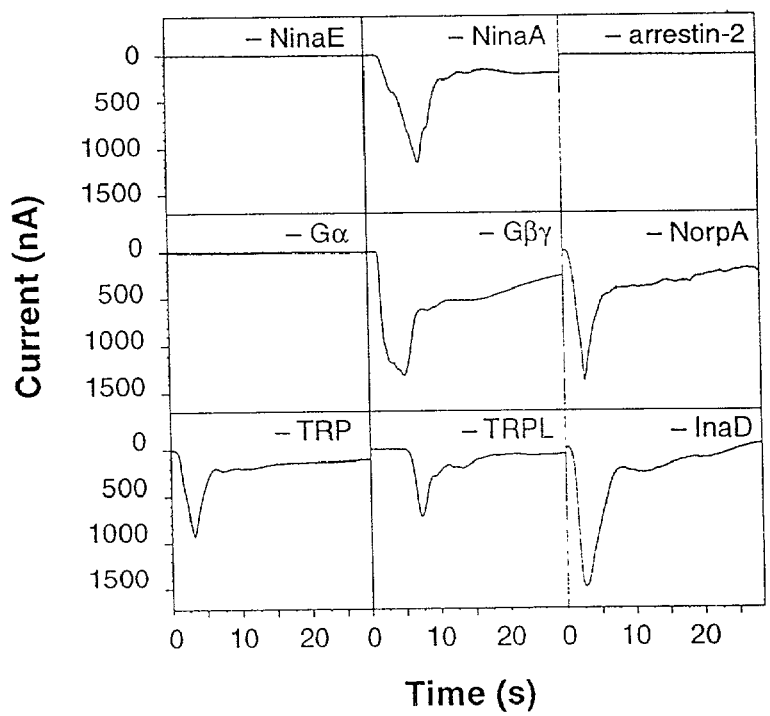
(FIG. 1B) "complete" sets deficient in the indicated single components. Although formally the product of two genes, the obligate Gβγ heterodimer is treated as a single entity.

The omission of any one of three mRNA species—those encoding NinaE, arrestin-2, and the G-protein α subunit, respectively—abolished the photocurrent; deficiencies in other mRNA species had no effect (FIG. 1B). The combination of the three essential phototransduction components alone was also sufficient to support the full amplitude of a photocurrent with identical pharmacological sensitivities (n=15 oocytes) (FIG. 1A). Rhodopsin and its immediate interacting partners (Ranganathan and Stevens, 1995; Montell, 1999), arrestin-2 and G$_q$α, thus constitute the minimal light-triggered "chARGe". Arrestin-2 presumably assists the conversion of metarhodopsin to rhodopsin (Kiselev and Subramaniam, 1994; Ranganathan and Stevens, 1995), while G$_q$α (which must assemble with an endogenous Gβγ dimer for function [Neer, 1995; Bohm et al., 1997]) couples activated NinaE to downstream effectors supplied by the oocyte.

The strict dependence on two auxiliary components, arrestin-2 and G$_q$α. NinaE from vertebrate rhodopsin, which by itself is able to trigger small photocurrents in oocytes (Khorana et al., 1988; Knox et al., 1993). While the two auxiliary components are essential for the function of NinaE, they in addition each contribute a unique and important feature to the mechanism of chARGe. G$_q$α provides a comparatively lossless interface between the light-activated receptor and its effectors, resulting in photocurrents that exceed those elicited by vertebrate rhodopsin in the same system (Khorana et al., 1988; Knox et al., 1993) by 10- to 100-fold. Arrestin-2, through its ability to stabilize the metarhodopsin form of NinaE (Kiselev and Subramaniam, 1994; Kiselev and Subramaniam, 1997), allows the molecule to be photoconverted back to rhodopsin. In the presence of arrestin-2, the photocycle of NinaE thus forms a closed loop that can regenerate the light-sensitive chromophore autonomously. The vertebrate rhodopsin, in contrast, depends on a steady supply of exogenous 11-cis retinal to replace the bleached all-trans isomer (Wald, 1968; Khorana et al., 1988; Rando, 1992; Knox et al., 1993).

EXAMPLE 5

The Requirement for Retinal

Figure 2:
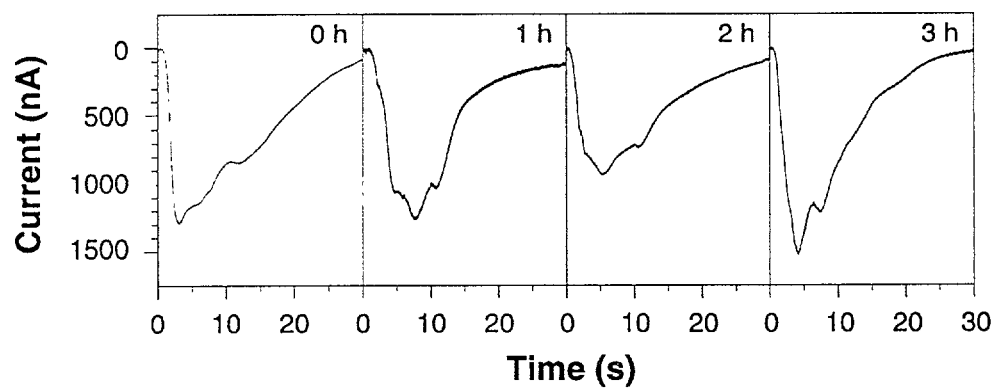
FIG. 2 shows the stability of chARGe after reconstitution of ninaE with retinal. Oocytes were programmed to express the minimal chARGe, consisting of NinaE, arrestin-2, and Gα, and exposed to 40 µM synthetic all-trans retinal for 15 min. At the end of the retinal load, the retinal-containing solution was displaced by a minimum of 10 chamber volumes of retinal-free extracellular recording solution, and the chamber was perfused with retinal-free recording solution throughout the remainder of the experiment. Light-evoked transmembrane currents were recorded at −80 mV after the indicated intervals following the retinal load. Inward currents are displayed as downward deflections from baseline; the zero time point is defined as the onset of the light stimulus.

Although its photocycle can operate autonomously once functional, chARGe requires an initial dose of retinal to reconstitute rhodopsin from empty, unliganded NinaE (FIG. 1A). Binding of retinal to opsin leads to the formation of a covalent Schiff base (Wald "The molecular basis of visual excitation," *Nature* 800–7. (1968)) between the chromophore and lysine-319 in the seventh transmembrane segment of NinaE (O'Tousa et al., 1985; Zuker et al., 1985). As a result, the initially reversible receptor-ligand equilibrium governed by mass action gives way to a stable association that is independent of the concentration of free ligand. For most practical purposes, a single saturating bolus of retinal should therefore be able to satisfy the chromophore requirement of NinaE permanently. Indeed, NinaE reconstituted with 40 µM synthetic all-trans retinal for 15 min remained functional for hours in the absence of exogenous retinal, with no attenuation of the photocurrent over time (n=8 oocytes) (FIG. 2).

EXAMPLE 6

Photostimulation of ChARGed Neurons

To examine its ability to transduce an optical stimulus into neuronal activity, the minimal chARGe (NinaE, arrestin-2, and $G_q\alpha$) was expressed in hippocampal neurons in primary culture. ChARGed neurons, identified by a co-transfected GFP marker (FIG. 3), were indistinguishable in differential interference contrast (DIC) from their untransfected counterparts and had identical resting membrane potentials, synaptic potentials, and rheobases (see below). Neither chARGed nor untransfected neurons in retinal-treated cultures showed signs of damage or death after exposure to stimulating light.

Figures 4A, 4B, 4C, 4D, 4E:
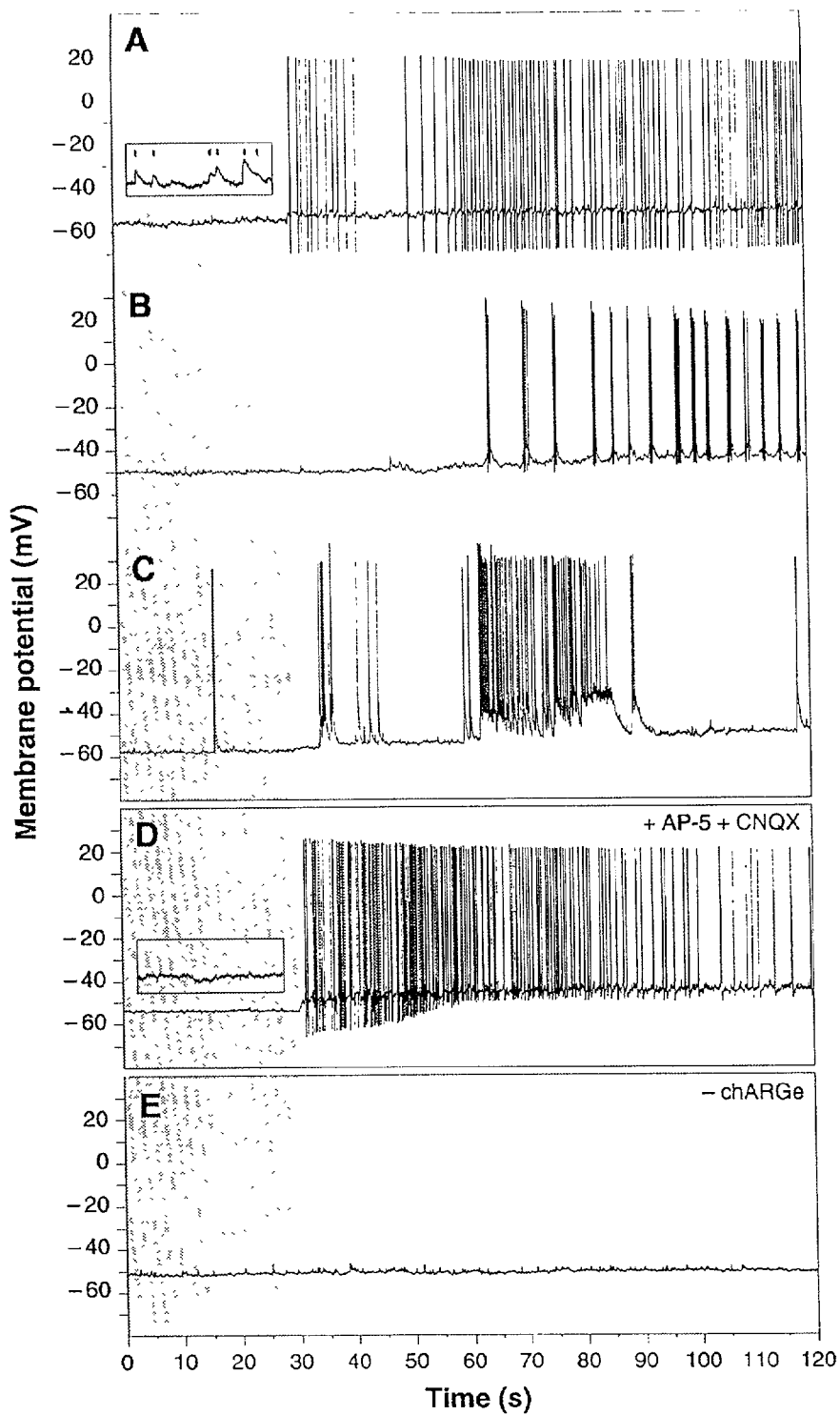
(FIG. 4A–FIG. 4D) Membrane potential records of four chARGed neurons, under conditions where excitatory synaptic transmission is intact (FIG. 4A–FIG. 4C) or blocked (FIG. 4D), reveal 86 (FIG. 4A), 86 (FIG. 4B), 59 (FIG. 4C), and 157 (FIG. 4D) light-evoked action potentials and spike latencies of 0.476 (FIG. 4A), 34.094 (FIG. 4B), 4.566 (FIG. 4C) and 1.330 s (FIG. 4D). Enlarged membrane potential traces (insets in FIG. 4A and FIG. 4D) show EPSPs (FIG. 4A, vertical marks) and their elimination by 50 µM AP-5 and 10 µM CNQX (FIG. 4D). Boxes surrounding the enlarged traces extend 5 mV vertically and 1 s horizontally.
FIG. 4E shows that an untransfected neuron incubated with retinal does not generate light-evoked action potentials but receives EPSPs at an increased frequency during illumination (2.08 $s^{-1}$ during illumination vs. 0.87 $s^{-1}$ in the dark). The increase in EPSP frequency indicates light-triggered activity in chARGed neurons that are presynaptic to the recorded, untransfected cell.

For intracellular recordings of light-evoked electrical activity, neurons were placed under whole-cell current clamp before reconstitution of NinaE with retinal. The membrane potential of chARGed neurons in the dark showed occasional excitatory postsynaptic potentials (EPSPs; FIG. 4A, inset), which exceedingly rarely summed to threshold (e.g., FIG. 4C). Exposure to white light increased the frequency of action potentials dramatically (FIGS. 4, A–D, and FIG. 5). Peak firing frequencies of 7.5 Hz (evaluated in sliding 2-s windows), equal to those generated by the direct injection of 200–250 pA of sustained depolarizing current into transfected and untransfected neurons, appeared after latency periods of a few hundred ms to several tens of s (n=18 neurons). In all likelihood, much of the cell-to-cell variation in light-triggered spike rates and spike latencies (FIGS. 4, A–D, and FIG. 5) was a consequence of the stochastic nature of transfection, which is expected to cause the absolute or relative levels of the three transiently expressed chARGe constituents (and, therefore, the cells' responsiveness to light) to fluctuate unpredictably from neuron to neuron. Stable integration of chARGe transgenes into the genomes of transgenic animals will reduce this variability.

Figure 5A:
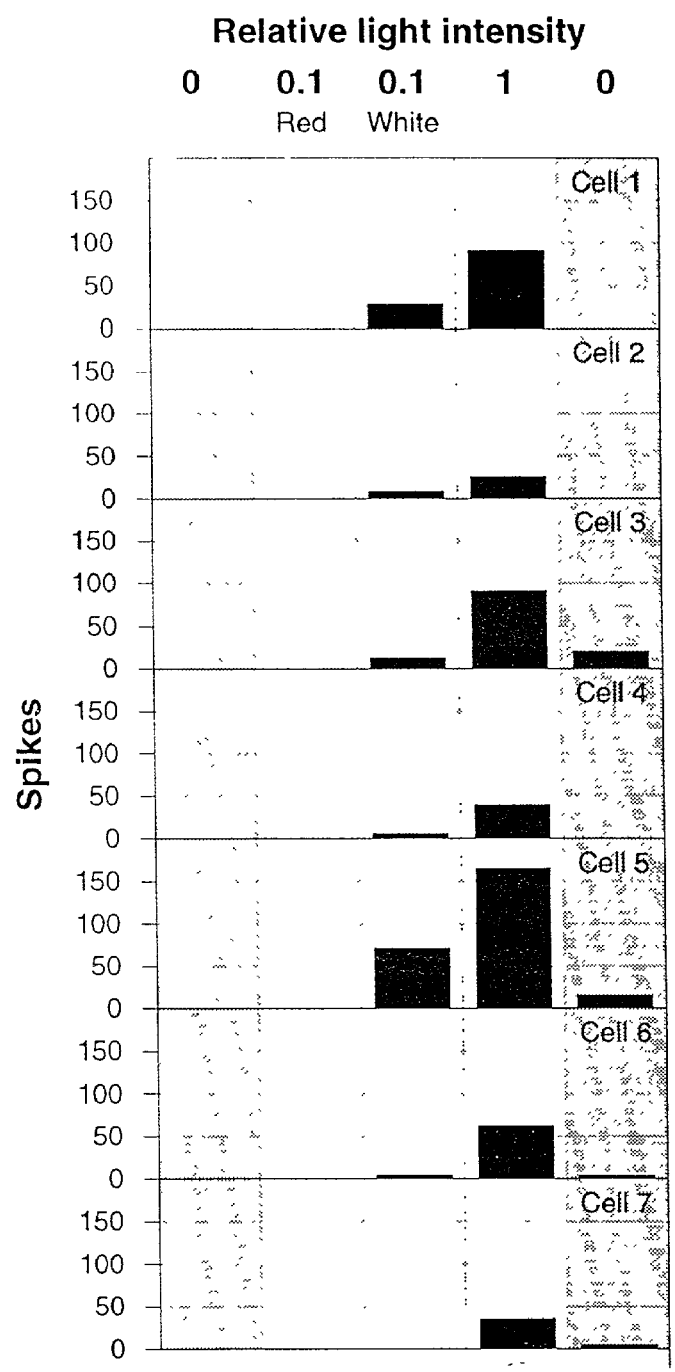
FIG. 5A: Histograms of spike counts in 7 neurons during consecutive 90-s episodes of darkness (relative light intensity=0), red illumination (relative light intensity~0.1), white illumination at relative intensities of 0.1 and 1, and darkness. A relative intensity of 1 corresponds to an optical power of 1.8 mW at the specimen. White light contains the wavelength band from 400 to 700 nm, red light the band from 605 to 645 nm (HQ625/40, Chroma), with a concomitant reduction in optical power to 0.15 mW (relative light intensity~0.1). A neutral density filter (UVND 1.0, Chroma) was used to attenuate the white spectrum to a comparable relative intensity of 0.1.

While cell-to-cell variation in gene dosage made comparisons at the population level difficult in the current experimental setting, a series of repeated measurements on individual chARGed neurons (n=7, FIG. 5) demonstrated clear relationships between the electrical response elicited in each of these neurons and the dose and energy of the photons incident on it. Action potentials increased in frequency at higher light intensities (FIG. 5A). At comparable intensities, photons needed to carry energies corresponding to visible wavelengths shorter than 600 nm to be effective (FIG. 5A). The band of effective wavelengths (400–600 nm; FIG. 5A) contains the absorption peak of native NinaE (430–550 nm; Hardie, 1983; Zuker et al., 1988).

Neuronal firing patterns under continuous illumination fell into two broad classes that echo the alternate operational modes accessible to many central neurons (McCormick et al., 1985; Llinás, 1988; Koch, 1999). Neurons in the first class (n=14) fired stand-alone action potentials with large after-hyperpolarizations (FIG. 4, A and D). Spikes occurred in "random" sequences with almost exponentially distributed interspike intervals (n=11 neurons; FIG. 4A and FIG. 6) or in the form of extended trains whose frequencies adapted (n=3 neurons; FIG. 4D). Action potentials of neurons in the second class (n=4) were always superimposed on slower depolarizing potentials; they either clustered in stereotyped high-frequency bursts of 4–9 spikes (n=2 neurons; FIG. 4B), or in irregularly timed epochs of variable duration and discharge intensity (n=2 neurons; FIG. 4C).

The observed electrical activity could be due to synaptic or autaptic (recurrent) excitatory inputs activated by an $IP_3$-induced rise in presynaptic $Ca^{2+}$. Alternatively, spikes could be initiated in a cell-autonomous manner. To distinguish between these mechanisms, glutamate receptors mediating excitatory synaptic transmission were blocked by 50 µM D,L-2-amino-5-phosphonovaleric acid (AP-5) and 10 µM 6-cyano-7-nitroquinoxaline-2,3-dione (CNQX) (n=5 neurons). As expected, EPSPs vanished from the membrane potential record (FIG. 4D, inset), but light-induced action potentials persisted (FIG. 4D). Consistent with a cell-autonomous mechanism of spike initiation, only genetically chARGed neurons, but not untransfected neurons in the same cultures (n=12), which are expected to receive similar synaptic input, fired light-evoked action potentials (FIG. 4E).

Figure 5B:
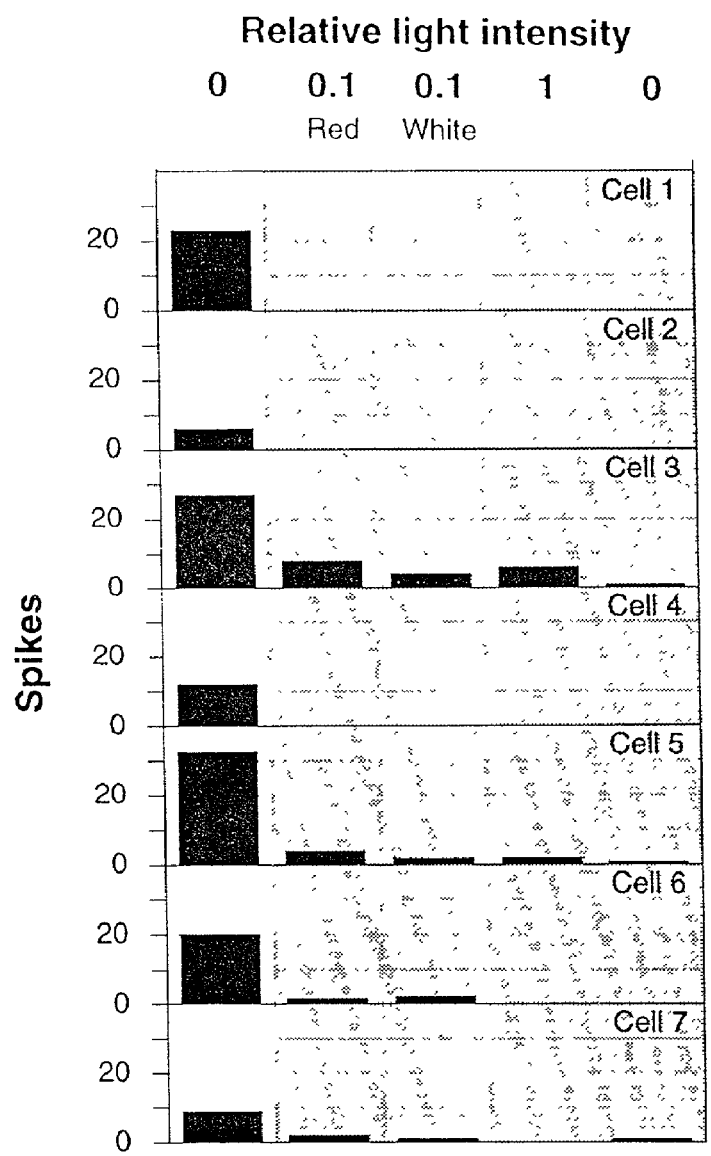
FIG. 5B: Histograms of spike counts in the 7 neurons displayed in panel A, showing the transition from light to darkness at higher temporal resolution. The five time bins cover the final 22.5 s of white illumination at relative intensity 1 and the subsequent 90-s dark period.
Figures 6A, 6B, 6C, 6D:
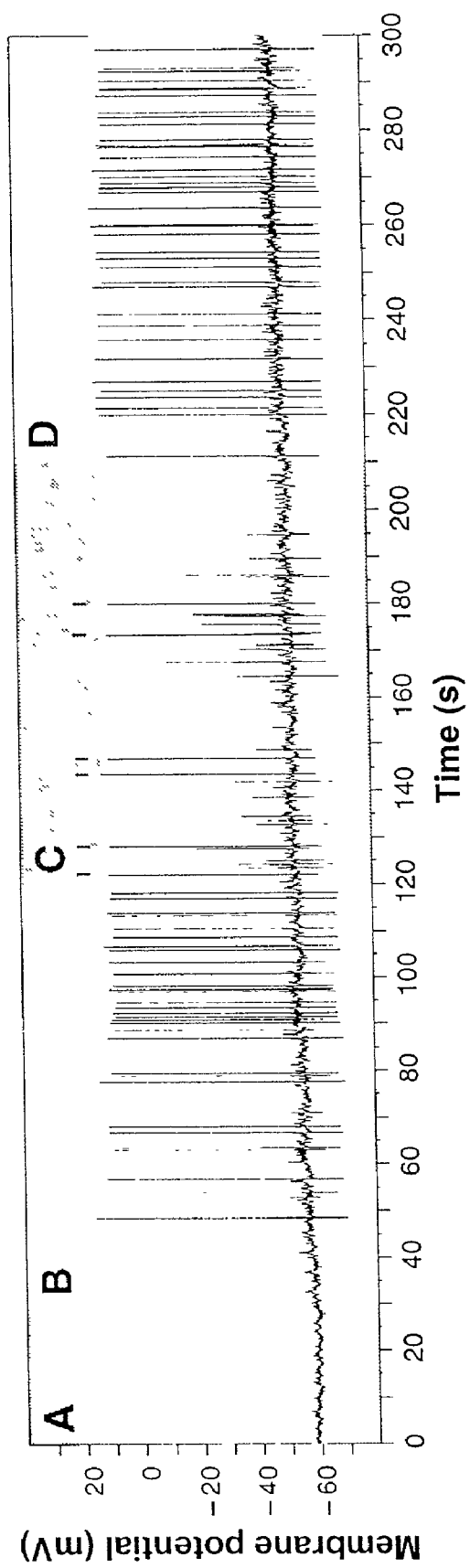
FIG. 6 shows a chARGed hippocampal neuron during alternating periods of darkness and illumination. Periods of darkness and white illumination are indicated by shaded and white backgrounds, respectively. The membrane potential record reveals 0 (FIG. 6A), 33 (FIG. 6B), 6 (FIG. 6C), and 40 (FIG. 6D) action potentials during the four consecutive episodes and "on" or "off" spike latencies of 18.091 (FIG. 6B, "on"), 58.860 (FIG. 6C, "off"), and 1.251 s (FIG. 6D, "on"). Activity during the dark period after the first stimulus consists of 6 full-scale spikes that invert the polarity of the membrane (FIG. 6C, vertical marks) and a number of lower-amplitude "spikelets". Spikelets, possibly dendritic action potentials triggered by residual chARGe activity, are seen in 67% of neurons (n=18) and in these cases constitute the most prominent form of spillover activity after a stimulus. They disappear during repeated illumination (FIG. 6D).

Alternating periods of light and darkness caused alternating episodes of electrical activity and quiescence (FIGS. 5 and 6). Action potentials often appeared and disappeared with lag periods after the light stimulus was applied (FIGS. 4B and 4C, and FIG. 6B) and removed (FIG. 5B and FIG. 6C). The tight temporal coupling between stimulus and response that characterizes the native photoreceptor (Hardie, 1991; Ranganathan et al., 1991; Scott and Zuker, 1998) thus seems relaxed in a chARGed neuron driven by only the minimal phototransduction machinery. Augmentation of the chARGe core with additional catalytic, structural or regulatory components (Scott and Zuker, 1997; Scott and Zuker, 1998; Montell, 1999), or fine adjustment of its stoichiometry (Ranganathan and Stevens, 1995), may be necessary to speed its response kinetics to photoreceptor timescales, and may eventually afford accurate control over spike times and firing frequencies.

EXAMPLE 7

*Drosophila melanogaster* Lines Expressing ChARGe Genes

Figure 7A:
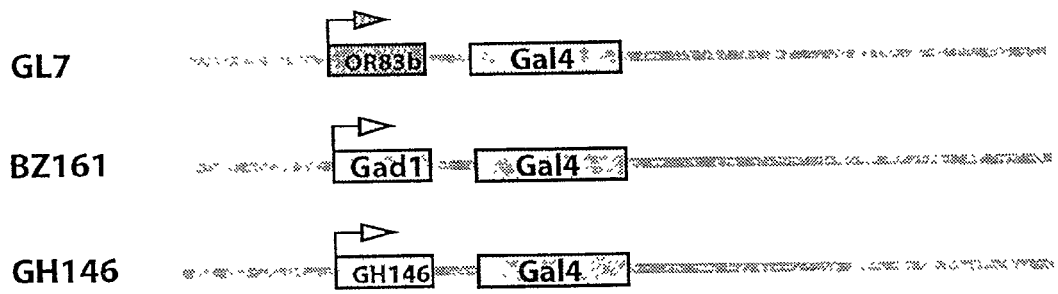
FIG. 7A illustrates a Gal4-UAS targeted gene expression system. A tissue-specific promoter is used to drive expression of the Gal4 gene; Gal4 expression is required for expression of the target gene of interest (Gene X), which is introduced downstream from five Gal4 binding sites (the UAS). Fly lines expressing the Gal4 protein in specific cells are crossed to lines carrying Gene X. The target gene is expressed in the offspring of the cross, only in the cells where Gal4 is present.
Figure 7A:
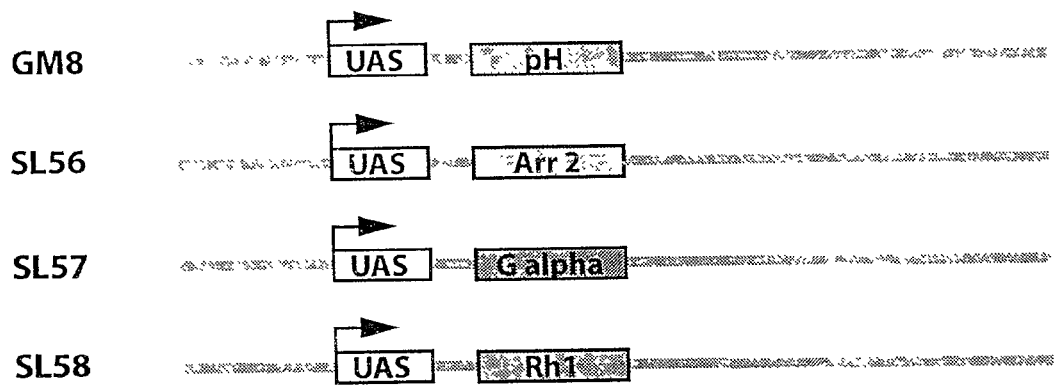
Figure 7B:
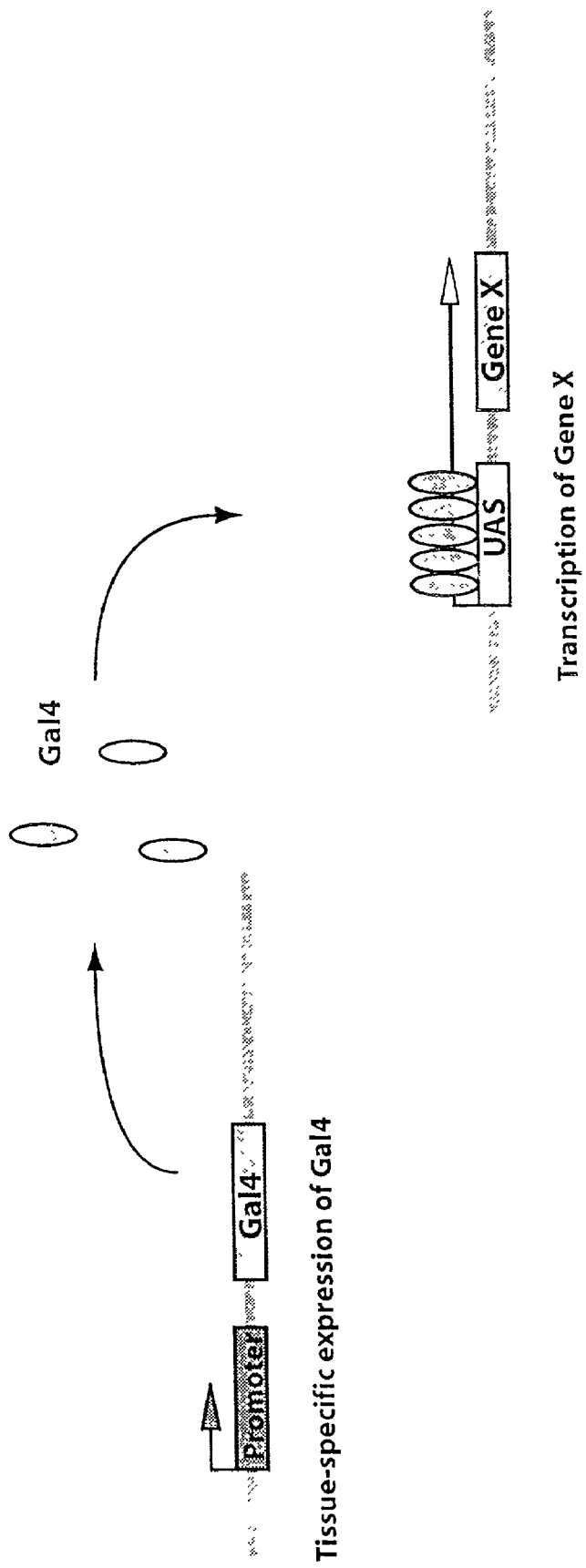
FIG. 7B illustrates the genotypes of fly lines either carrying the Gal4 gene under control of a cell type-specific driving promoter (pGal4—3 independent fly lines), and one fly line carrying all the chARGe silent genes (pUAS).
Figure 7C:
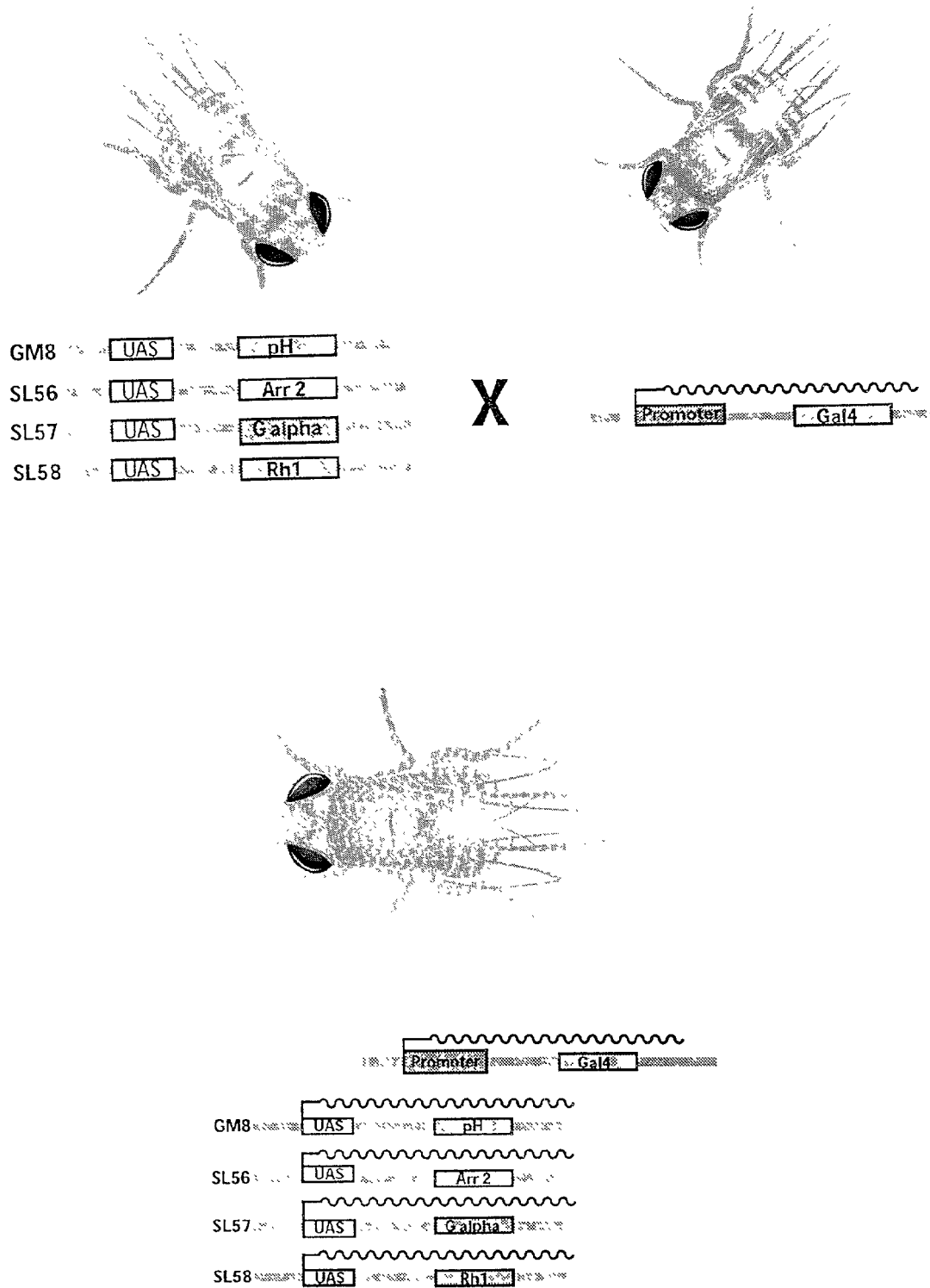
FIG. 7C illustrates a cross between one of the pGal4 and the pUAS fly lines to create a line expressing all of the chARGe genes. Flies carrying the chARGe genes (synapto-pHluorin neural activity sensor (see below), arrestin-2, G-alpha, and ninaE) and one of the cell-specific drivers (pGal4 vectors) are mated. In these flies NinaE protein has an additional 10 amino acids (myc-tag) at the N-terminus to allow it to be detected with an antibody raised against the amino acid tag and distinguished from the endogenous NinaE protein. The expression pattern of the four genes in the progeny is then identical to that of the driver.

*Drosophila* lines expressing the Gal4 protein in specific cells were crossed to lines carrying the target gene of interest (Gene X) subcloned downstream from five Gal4-binding sites (the UAS); see FIG. 7A. The target gene is expressed in the offspring of the cross, only in the cells where Gal4 is present. Flies carrying the chARGe genes (pH, Arr2, G alpha and ninaE) and one of the cell-specific drivers (pGal4 vectors) were mated. The expression pattern of the four genes in the progeny is then identical to that of the driver; see FIGS. 7B and 7C.

Figure 7D:
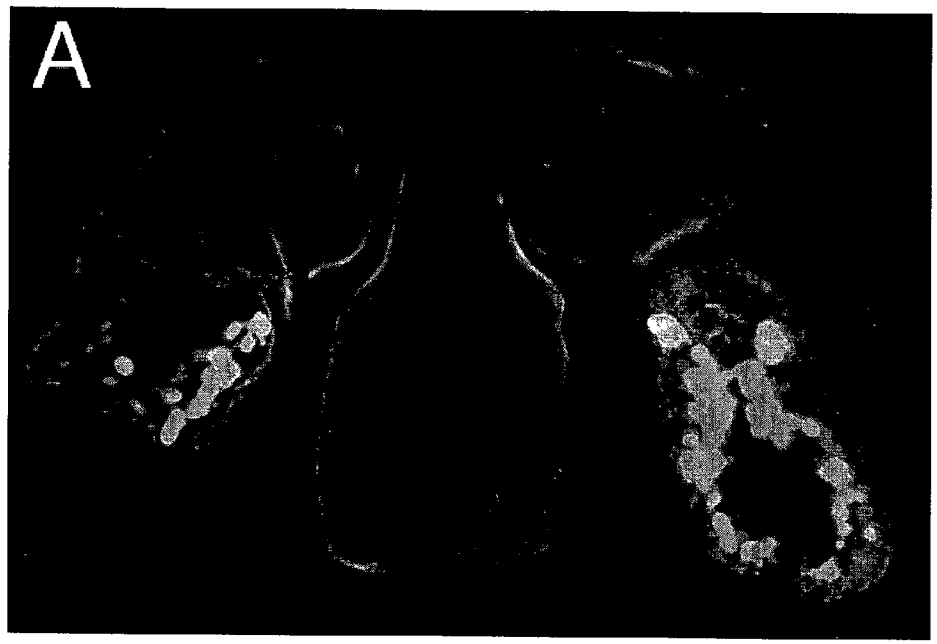
FIG. 7D illustrates expression of chARGe transgenes in Drosophila. Flies carrying (A) UAS-rhodopsin, (B) UAS-arrestin-2, and (C) UAS-$G_q\alpha$ transgenes were crossed with the olfactory receptor neuron (ORN)-specific driver DOR83-GAL4. Expression of chARGe transgenes was detected in frozen antennal sections. (A) Immunostaining with a monoclonal anti-myc antibody reveals expression of myc-tagged rhodopsin protein in olfactory receptor neurons. (B,C) In situ hybridization with cognate antisense ribo-probes reveals expression of arrestin-2 (B) and $G_q\alpha$ (C) mRNA in olfactory receptor neurons.
Figure 7D:
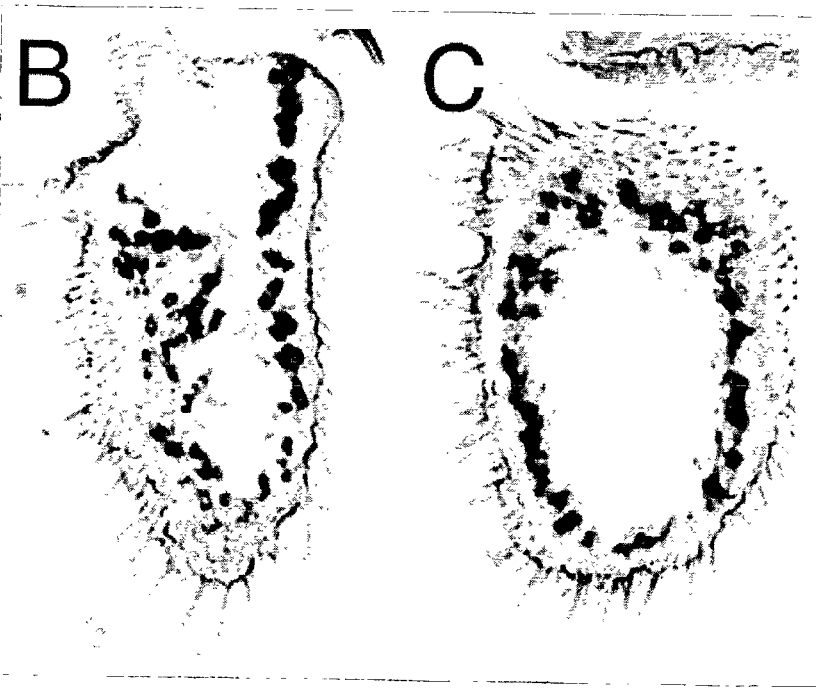

Transformant lines were generated using standard procedures (Spradling and Rubin "Transposition of cloned P elements into *Drosophila* germ line chromosomes," *Science* 341–7 (1982)). Embryos of the *Drosophila melanogaster* yellow white strain were injected with plasmid DNA containing each transgene along with a phenotypic marker. Surviving flies were crossed with wild type y w flies and their progeny were screened for the presence of the phenotypic marker. The presence of the transgene was then confirmed using PCR analysis. Flies carrying all four transgenes were generated with recombinational crosses by screening for the phenotypic traits co-segregating with each of the transgenes. The presence of the four transgenes in the recombinant flies was confirmed by PCR, in situ hybridization, and immunofluorescence (FIG. 7D). Flies carrying the four transgenes were then crossed with the driver lines, leading to the expression of chARGe transgenes in designated neuron populations.

The GL7 Gal4 driver fly line uses 7.087 kb of sequence immediately upstream of the putative translation codon of OR83b (an olfactory receptor gene that is expressed in a large (~70%) population of olfactory receptor neurons) to drive the expression of Gal4.

The GAD1 Gal4 driver fly line uses 3.098 kb of sequence immediately upstream of the putative translation codon of GAD1 (the gene encoding the key enzyme in GABA biosynthesis, glutamic acid decarboxylase, that is expressed in GABAergic inhibitory local neurons) to drive the expression of Gal4.

The GH146 Gal4 driver fly line uses a uses an unknown regulatory sequence to drive Gal4 expression in projection neurons (Stocker, Heimbeck et al. "Neuroblast ablation in *Drosophila* P[GAL4] lines reveals origins of olfactory interneurons," *J Neurobiol* 443–56 (1997)). This is an enhancer trap line, meaning that the P-element transposon carrying the Gal4 gene was inserted randomly into the fly genome. Gal4 expression was subsequently shown to take place in the projection neurons.

EXAMPLE 8

Viral chARGe Expression Vectors

Figure 8A:
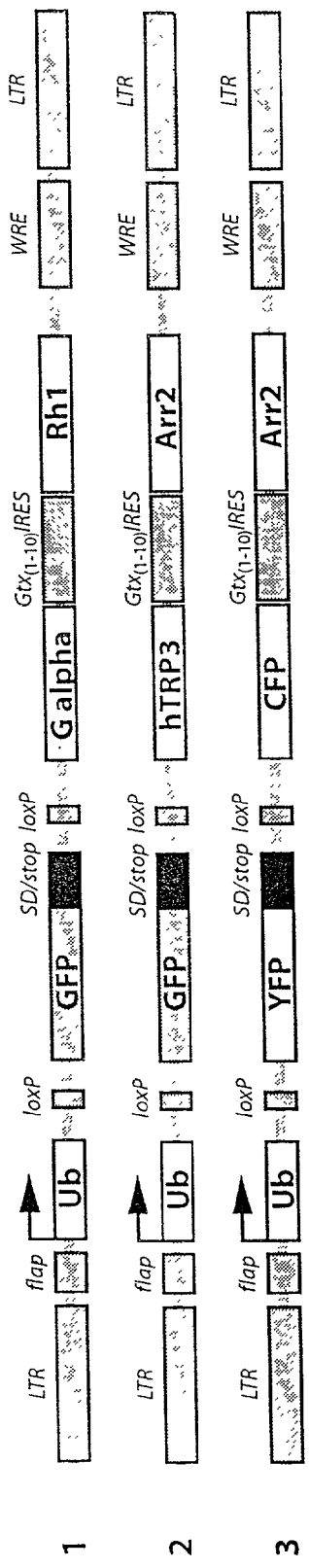
FIG. 8a shows two sets of constructs containing chARGe genes. The pvChARGe loxSD 1–3 constructs contain stop cassettes that prevent translation of the chARGe genes unless Cre recombinase is present, as illustrated in FIG. 8b. These constructs may also contain a fluorescent protein gene (GFP, YFP, HcRed, DsRed2, or CFP) that enables identification of transfected cells. The fluorescent proteins have different fluorescent properties, so that they can be independently tracked in the same tissue preparation (Feng, Mellor et al. "Imaging neuronal subsets in transgenic mice expressing multiple spectral variants of GFP," Neuron 41–51. (2000)).
Figure 8A:
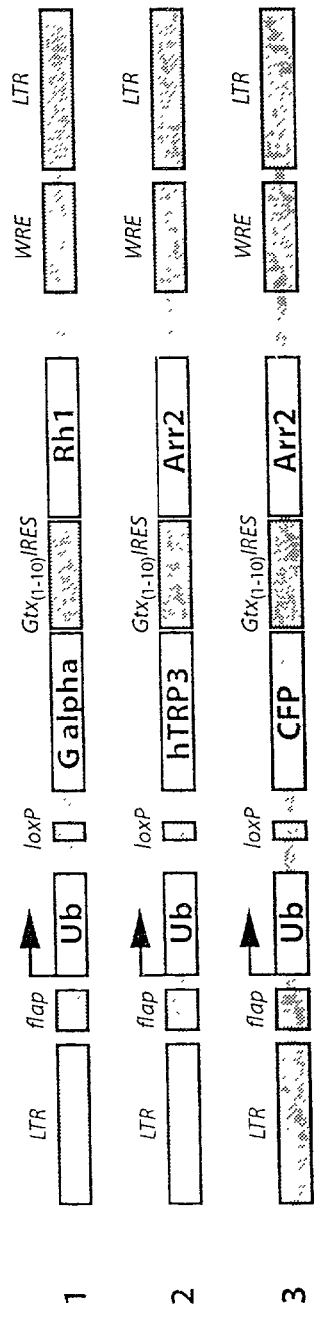
Figure 8B:
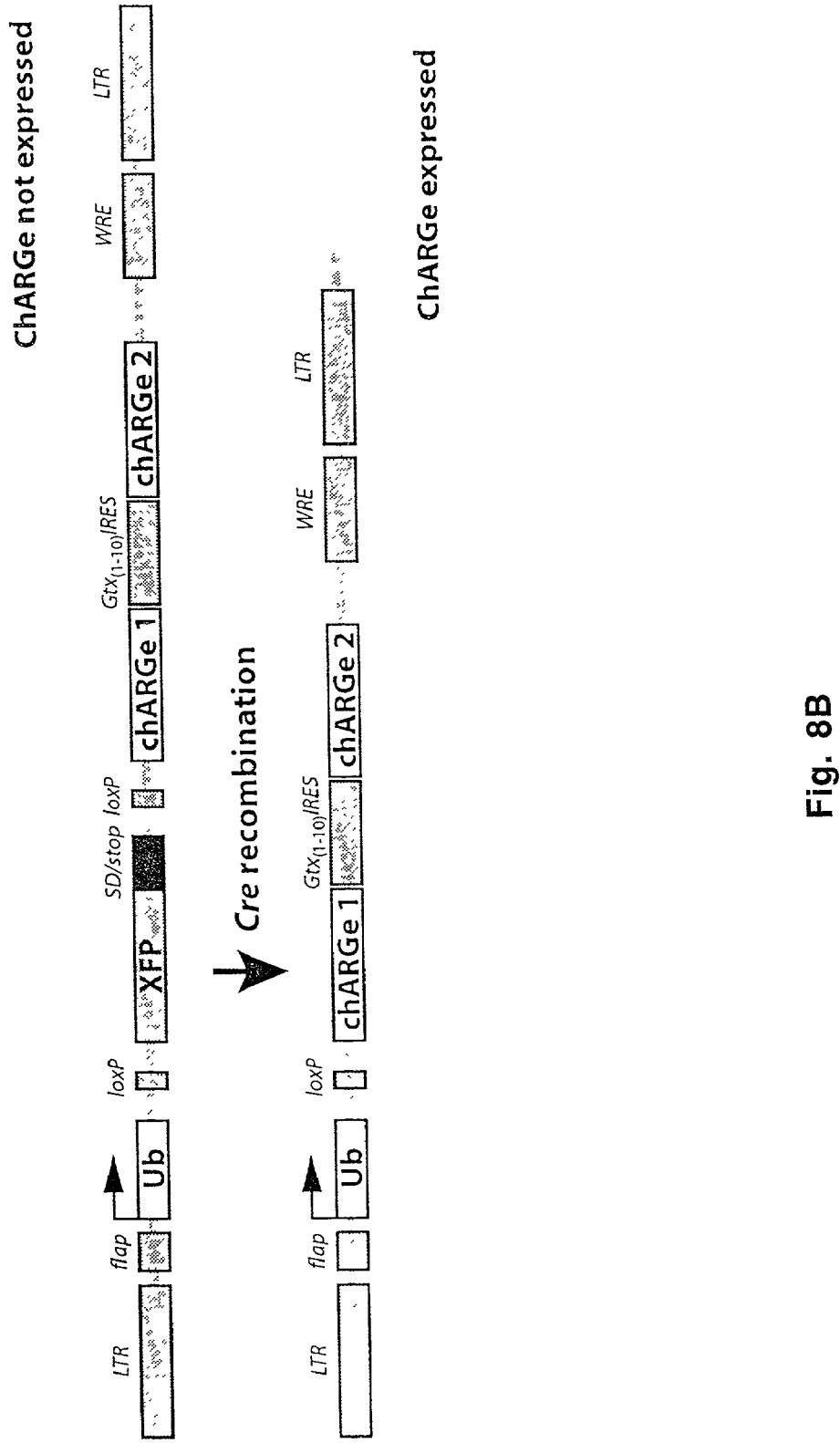
In FIG. 8b, "chARGe 1" and "chARGe2" denote the "minimum chARGe" genes (opsin, arrestin-2, and the alpha subunit of a heterotrimeric G protein).

In the constructs as shown in FIGS. 8A and 8B, the Ubiquitin promoter is active in all cells, but the STOP cassette prevents the translation of the genes downstream of the STOP. Only in cells also expressing the Cre recombinase is the STOP removed, allowing transgene expression in a spatially-restricted manner. Virus with the STOP cassette can be used to infect Cre-expressing tissues of an animal. Alternatively, a transgenic animal containing the STOP construct in all cells can be mated with an animal expressing Cre recombinase in specific cells to generate transgenically active progeny. Via the action of Cre recombinase, the fluorescent protein gene would be removed, and chARGe genes would be expressed. A two-part approach may be used. In such an approach, first all cells are infected, i.e., are identifiable by detection of fluorescence of the expressed fluorescent protein. Second, by keeping track of Cre recombinase, it can be known which neurons will become chARGed. Because whole fields of cells may be stimulated, it is not necessary to know exactly which cells are chARGed; these may be detected subsequently using antibodies against any or all of the relevant expressed proteins.

Construction of the viral vectors was performed by introducing a cloning cassette between the BamH1 and EcoR1 restriction sites of an existing lentivirus vector FUGW (Lois, Hong et al. "Germline transmission and tissue-specific expression of transgenes delivered by lentiviral vectors," *Science* 868–72. (2002)). The cassette contained the following restriction sites, in order: BsiW1-Asc1-Csp1. Two chARGe genes were inserted into the Asc1 site, forming a PinA1 site between them. IRES sequence was inserted into the PinA1 site. Lox-color-STOP-lox was then inserted into the BsiW1 site, creating the final vector. The Csp1 site provides room for an additional gene or color marker, if necessary. Vectors were also contructed without the loxP cassette, to be used for unrestricted gene expression find for control experiments. Active virus particles were constructed using the vectors and helper plasmids in 293T cells as previously described.

EXAMPLE 9

TRPC3

The combination of the three essential phototransduction components alone was sufficient to support a substantial photocurrent in oocytes and neurons. To determine whether the inclusion of TRPC3, the human isoform of the *Drosophila* TRP channel that is hypothesized to be activated by the second messengers produced following photostimulation of chARGed cells, oocytes were programmed with mRNA pools encoding the three chARGe proteins or the three chARGe proteins and TRPC3. Three days after mRNA injection the oocytes were incubated in the dark with all-trans retinal and subsequently photostimulated, as described above. As shown in FIG. 9, the oocytes programmed with the three chARGe proteins and TRPC3 exhibited a stronger photocurrent than did the oocytes programmed with the three chARGe proteins alone.

The principle illustrated by chARGe promises to relieve serious impediments to neurobiological discovery, in many systems and experimental circumstances. Two examples are highlighted. In vivo, sensory interfaces have provided the sole portals through which distributed inputs could be supplied to neural circuits. Because these inputs are repeatedly re-formatted in intervening processing stages, the exact signals reaching a neuron or circuit at some synaptic distance from the sensory surface are often obscure. Attempts in psychophysics to solve this problem by "operationally 'skipping' the peripheral processes and stimulating some central location" (Julesz "Foundations of Cyclopean perception," 406 (1971)) have remained limited to sensory systems, and constrained in their inability to connect the observed phenomena back to their cellular foundation. ChARGe removes these constraints. Synthetic neural signals can now be inserted with high precision into virtually any location in any neural pathway of a transgenic animal and the behavioral or developmental consequences of such interventions explored.

Equally powerful applications are possible in vitro. By their very nature, explanted neural tissues such as cortical or hippocampal slices are stripped of all external connections, and no controlled way has existed to probe their circuitry with distributed inputs. Broad illumination of slices obtained from the brains of transgenic animals can now elicit population activity in a precisely defined class of chARGed neurons, or even in multiple classes independently that are each chARGed with a distinct spectral variant (Hardie "Functional organization of the fly retina," *Progress in Sensory Physiology* 1–79 (1983; Montell "Visual transduction in *Drosophila*," *Annu Rev Cell Dev Biol* 231–68 (1999)) of NinaE. The spread of these synthetic test patterns and the transformations imposed on them by neural circuits can be traced in optical or multielectrode recordings, to reveal the underlying functional architectures and computational principles.

The following references were cited herein:

Bloomquist, et al., (1988). Cell 54, 723–733.
Bohm, et al., (1997). Curr Opin Biotechnol 8, 480–487.
Burns, et al., (2001). Annu Rev Neurosci 24, 779–805.
Byk, et al., (1993). Proc Natl Acad Sci USA 90, 1907–1911.
Callaway, et al., (1993). Proc Natl Acad Sci USA 90, 7661–7665.
Colicos, et al., (2001). Cell 107, 605–616.
Crick, F. (1999). Phil. Trans R Soc Lond Biol Sci 354, 2021–2025.
Dalva, M. B., and Katz, L. C. (1994). Science 265, 255–258.
Denk, W. (1994). Proc Natl Acad Sci USA 91, 6629–6633.
Farber, I. C., and Grinvald, A. (1983) Science 222, 1025–1027.
Fromherz, et al., (1995). Phys Rev Lett 75, 1670–1673.
Gafni, et al., (1997). Neuron 19, 723–733.
Hardie, R. (1983). Functional organization of the fly retina. In Progress in Sensory Physiology, D. Ottoson, ed. (Berlin, Springer-Verlag), pp. 1–79.
Hardie, R. C. (1991). Proc R Soc Lond B 245, 203–210.
Hardie, R. C., and Minke, B. (1992). Neuron 8, 643–651.
Hardie, R. C., and Raghu, P. (2001). Nature 413, 186–193.
Hillman, et al., (1983). Physiol Rev 63, 668–772.
Huber, et al., (1996). EMBO J 15, 7036–7045.
Hyde, et al., (1990). Proc Natl Acad Sci USA 87, 1008–1012.
Inoue et al., (1985) Biochem Bioph. Res Commun 132, 513–519.
Julesz, B. (1971). Foundations of Cyclopean perception (Chicago, The University of Chicago Press).
Khorana, et al., (1988). Proc Natl Acad Sci USA 85, 7917–7921.
Kiselev, et al., (1994). Science 266, 1369–1373.
Kiselev, et al., (1997). Biochemistry 36, 2188–2196.
Knox, et al., (1993). J Physiol (Lond) 466, 157–172.
Koch, C. (1999). Biophysics of computation. (New York—Oxford, Oxford University Press).
Kovacs, G. (1994). Introduction to the theory, design, and modeling of thin-film microelectrodes for neural interfaces. In Enabling technologies for cultured neural networks, Stenger, and T. McKenna, eds. (San Diego, Academic Press), pp. 121–165.
Lee, et al., (1990). Neuron 5, 889–898.
LeVine, et al., (1990). Mech Dev 33, 19–25.
Liman, E. R., Tytgat, J., and Hess, P. (1992). Neuron 9, 861–871.
Llinás, R. R. (1988). Science 242, 1654–1664.
Matsuzaki, et al., (2001). Nature Neurosci 4, 1086–1092.
McCormick, et al., (1985). J Neurophysiol 54, 782–806.
Montell, C. (1999). Visual transduction in *Drosophila*. Annu Rev Cell Dev Biol 15, 231–268.
Montell, C., and Rubin, C. (1989). Neuron 2, 1313–1323.
Moriyoshi, et al., (1996). Neuron 16, 255–260.
Neer, E. J. (1995). Cell 80, 249–257.
O'Tousa, et al. (1985). Cell 40, 839–850.
Penfield, W., and Rasmussen, T. (1950). The cerebral cortex of man. A study of localization of function. (New York, Macmillan).
Pettit, et al., Neuron 19, 465–471.
Phillips, et al., (1992). Neuron 8, 631–642.
Pine, J. (1980). J Neurosci Methods 2, 19–31.
Rando, R. R. (1992). Photochem Photobiol 56, 1145–1156.
Ranganathan, et al., (1991). Nature 354, 230–232.
Ranganathan, R., and Stevens, C. F. (1995). Cell 81, 841–848.
Regehr, et al., (1989)). J Neurosci Methods 30, 91–106.
Salzman, et al., (1990) Nature 346, 174–177.
Schulz, et al., (1999). J Biol Chem 274, 37605–37610.
Scott, K., and Zuker, C. (1997). Trends Biochem Sci 22, 350–354.
Scott, K., and Zuker, C. S. (1998). Nature 395, 805–808.
Shieh, B. H., and Niemeyer, B. (1995). Neuron 14, 201–210.
Shieh, et al., (1989). Nature 338, 67–70.
Stryer, L. (1991). J Biol Chem 266, 10711–10714.
Tsunoda, et al., (1997). Nature 388, 243–249.
Vogt, et al., (1984). Naturwissenschaften 71, 211–213.
Wald, G. (1968). Nature 219, 800–807.
Yamada, et al., (1990). Science 248, 483–486.
Yarfitz et al., (1991). Neuron 7, 429–438.
Yuste, et al., (2000). Methods Enzymol 327, 522–546.
Zemelman and Miesenböck (2001) Curr Opin Neuro 11, 409–414.
Zuker, et al., (1985). Cell 40, 851–858.
Zuker, et al., (1988). Cell 53, 475–482.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of sensitizing a cell to light, comprising the steps of: (a) introducing into the cell a nucleic acid encoding an opsin gene product, a nucleic acid encoding an arrestin gene product, and a nucleic acid encoding the alpha subunit of a heterotrimeric G protein; so that the opsin gene product, the arrestin gene product, and the alpha subunit of a heterotrimeric G protein are expressed in said cell; and (b) contacting said cell with retinal or a derivative thereof so as to convert said opsin gene product into a rhodopsin, wherein the method is performed in vitro, the cell is a neuron, the heteromeric C protein encoded by the nucleic acid comprises a *Drosophila melanogster* $G_q\alpha$ protein, the arrestin gene product is an arrestin-2 gene product of *Drosphila melanogaster* and the opsin gene product is selected from the group consisting of an insect opsin gene product, a *Drosophila* opsin gene product, ninaE and engineered variants of an opsin gene product.

2. The method of claim 1, wherein said derivative of retinal is 3-hydroxyretinal.

3. The method of claim 1, wherein said derivative of retinal is selected from the group consisting of 3-hydroxyretinal, retinol, 3-hydroxyretinol, retinyl ester and 3-hydroxyretinyl ester.

4. The method of claim 1, wherein each nucleic acid is operatively linked to a promoter which is active in the cell.

5. The method of claim 4, wherein said promoter is selected from the group consisting of a non-specific promoter for said cell and a cell-specific promoter for said cell.

6. The method of claim 5, further comprising an internal ribosome entry site sequence operatively linked to the promoter.

7. The method of claim 1, wherein said introducing is by transfection.

8. The method of claim 7, wherein said transfection comprises transfecting the cell with two or more different species of plasmids.

9. The method of claim 8, wherein one plasmid is pChARGe-1 and the second plasmid is pChARGe-2.

10. The method of claim 1, wherein said introducing comprises infecting the cell with a virus comprising said nucleic acid sequences.

11. A method of photostimulating a non-photoreceptor cell, comprising the steps of: (a) introduction into the cell a nucleic acid encoding an opsin gene product, a nucleic acid encoding an arrestin gene product, and a nucleic acid encoding the alpha subunit of a heterotrimeric G protein; so that the opsin gene product, the arrestin gene product, and the alpha subunit of a heterotrimeric G protein are expressed in said cell; (b) contacting said cell with retinal or a derivative thereof so as to convert said opsin gene product into a rhodopsin; and (c) illuminating the cell with light having a wavelength capable of transforming said rhodopsin into a metarhodopsin whereby said metarhodopsin activates said heterotrimeric G protein, wherein the method is performed in vitro, the cell is a neuron, the heteromeric G protein encoded by the nucleic acid comprises a *Drosophila melanogster* $G_q\alpha$ protein, the arrestin gene product is an arrestin-2 gene product of *Drosphila melanogaster* and the opsin gene product is selected from the group consisting of an insect opsin gene product, a *Drosophila* opsin gene product, ninaE and engineered variants of an opsin gene product.

* * * * *

UNITED STATES PATENT AND TRADEMARK OFFICE
CERTIFICATE OF CORRECTION

PATENT NO. : 7,144,733 B2
APPLICATION NO. : 10/222675
DATED : December 5, 2006
INVENTOR(S) : Miesenbock et al.

It is certified that error appears in the above-identified patent and that said Letters Patent is hereby corrected as shown below:

In the claims: Col. 30

Claim 1, Line 61 should read: --heteromeric G protein encoded by the nucleic acid comprises--

Signed and Sealed this

Sixth Day of February, 2007

JON W. DUDAS
*Director of the United States Patent and Trademark Office*